US009891236B2

(12) United States Patent
Breton et al.

(10) Patent No.: US 9,891,236 B2
(45) Date of Patent: Feb. 13, 2018

(54) COMPOSITIONS AND METHODS FOR DETECTING AND/OR TREATING INFLAMMATION

(71) Applicant: THE GENERAL HOSPITAL CORPORATION, Boston, MA (US)

(72) Inventors: Sylvie Breton, Belmont, NH (US); Dennis Brown, Natick, MA (US); Anie Azroyan, Boulogne-Billancourt (FR); Virna F. Cortez-Retamozo, Cambridge, MA (US); Mikael Pittet, Charlestown, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 89 days.

(21) Appl. No.: 15/035,033

(22) PCT Filed: Nov. 7, 2014

(86) PCT No.: PCT/US2014/064525
§ 371 (c)(1),
(2) Date: May 6, 2016

(87) PCT Pub. No.: WO2015/070001
PCT Pub. Date: May 14, 2015

(65) Prior Publication Data
US 2016/0274131 A1    Sep. 22, 2016

Related U.S. Application Data

(60) Provisional application No. 61/962,476, filed on Nov. 7, 2013, provisional application No. 61/931,184, filed on Jan. 24, 2014, provisional application No. 61/931,146, filed on Jan. 24, 2014.

(51) Int. Cl.
G01N 33/53     (2006.01)
G01N 33/74     (2006.01)
G01N 33/566    (2006.01)
G01N 33/66     (2006.01)
A61K 31/451    (2006.01)
C07K 16/28     (2006.01)
A61K 39/00     (2006.01)

(52) U.S. Cl.
CPC .......... *G01N 33/74* (2013.01); *A61K 31/451* (2013.01); *C07K 16/28* (2013.01); *G01N 33/5308* (2013.01); *G01N 33/566* (2013.01); *G01N 33/66* (2013.01); *A61K 2039/505* (2013.01); *C07K 2317/20* (2013.01); *C07K 2317/76* (2013.01); *G01N 2333/726* (2013.01); *G01N 2800/347* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

2006/0134109 A1    6/2006  Gaitanaris et al.

FOREIGN PATENT DOCUMENTS

WO    03/076945 A2    9/2003
WO    2013/033178 A1  3/2013

OTHER PUBLICATIONS

Harden et al. Acta Physiol 2010 vol. 199, p. 149-160.*
J. Biol. Chem. 2009 vol. 284, p. 12572-12583.*
Arase et al., "The UDP-Glucose Receptor P2RY14 Triggers Innate Mucosal Immunity in the Female Reproductive Tract by Inducing IL-8", The Journal of Immunology 182:7074-7084 (2009).
Barrett et al., "A Selective High-Affinity Antagonist of the P2Y14 Receptor Inhibits UDP-Glucose-Stimulated Chemotaxis of Human Neutrophils", Molecular Pharmacology 84:41-49 (2013).
Breton et al., "Regulation of Luminal Acidification by the V-ATPase", Physiology 28:318-329 (2013).
Chambers et al., "A G Protein-coupled Receptor for UDP-glucose", The Journal of Biological Chemistry 275(15):10767-10771 (2000).
Chen et al., "ATP Release Guides Neutrophil Chemotaxis via P2Y2 and A3 Receptors", Science 314:1792-1795 (2006).
Chen et al., "Sterile inflammation: sensing and reacting to damage", Nat Rev Immunol. 10(12):826-837 (2010).
Dovlatova et al., "Detection of P2Y14 protein in platelets and investigation of the role of P2Y14 in platelet function in comparison with the EP3 receptor", Thromb Haemost 100:261-270 (2008).
Elliott et al., "Nucleotides released by apoptotic cells act as a find-me signal for phagocytic clearance", Nature 461 (7261):282-286 (2009).
Fricks et al., "Gi-Dependent Cell Signaling Responses of the Human P2Y14 Receptor in Model Cell Systems", The Journal of Pharmacology and Experimental Therapeutics 330(1):162-168 (2009).
Gao et al., "UDP-glucose acting at P2Y14 receptors is a mediator of mast cell degranulation", Biochem Pharmacol. 79(6):873-879 (2010).
Gauthier et al., "The identification of 4 7-disubstituted naphthoic acid derivatives as UDP-competitive antagonists of P2Y14", Bioorganic Medicinal Chemistry Letters 21:2836-2839 (2011).
Harden et al., "Signalling and pharmacological properties of the P2Y14 receptor", Acta Physiol (Oxf) 199(2):149-160 (2010).
Lazarowski et al., "Nucleotide Release by Airway Epithelia", Subcellular Biochemistry 55:1-15 (2011).

(Continued)

Primary Examiner — Changhwa J Cheu
(74) Attorney, Agent, or Firm — Mark J. FitzGerald; Teresa A. Ptashka; Nixon Peabody LLP

(57) ABSTRACT

The present disclosure relates to assays and methods for the detection of renal inflammation by measuring the level of P2Y14 and/or UDP-glucose in a sample from a subject, such as a urine sample. The present disclosure also relates to methods for the treatment of renal inflammation by administering a P2Y14 inhibitor.

19 Claims, 18 Drawing Sheets

(56) References Cited

OTHER PUBLICATIONS

Lazarowski et al., "Release of Cellular UDP-Glucose as a Potential Extracellular Signaling Molecule", Molecular Pharmacology 63(5):1190-1197 (2003).

Leipziger et al., "Luminal nucleotides are tonic inhibitors of renal tubular transport", Current Opinion Nephrology and Hypertension 20:518-522 (2011).

Moore et al., "GPR105, a novel Gi/o-coupled UDP-glucose receptor expressed on brain glia and peripheral immune cells, is regulated by immunologic challenge: possible role in neuroimmune function", Molecular Brain Research 118:10-23 (2003).

Muller et al., "The P2Y14 Receptor of Airway Epithelial Cells: Coupling to Intracellular Ca2+ and IL-8 Secretion", Am J Respir Cell Mol Biol 33:601-609 (2005).

Scrivens et al., "Functional expression of the P2Y14 receptor in human neutrophils", European Journal of Pharmacology 543:166-173 (2006).

Scrivens et al., "Functional expression of the P2Y14 receptor in murine T-lymphocytes", British Journal of Pharmacology 146:435-444 (2005).

Sesma et al., "Endoplasmic Reticulum/Golgi Nucleotide Sugar Transporters Contribute to the Cellular Release of UDP-sugar Signaling Molecules", The Journal of Biological Chemistry 284(18):12572-12583 (2009).

Wagner et al., "Renal Vacuolar H+-ATPase", Physiol Rev. 84:1263-1314 (2004).

Zimmermann, "Extracellular metabolism of ATP and other nucleotides", Naunyn-Schmiedeberg's Arch Pharmacol 362:299-309 (2000).

Azroyan et al., "Renal intercalated cells sense and mediate inflammation via the P2Y14 receptor", PLoS One 10(3) e0121419 (2015).

Awad et al., "Compartmentalization of neutrophils in the kidney and lung following acute ischemic Kidney injury", Kidney Int 75(7), 689-698, 2009.

\* cited by examiner

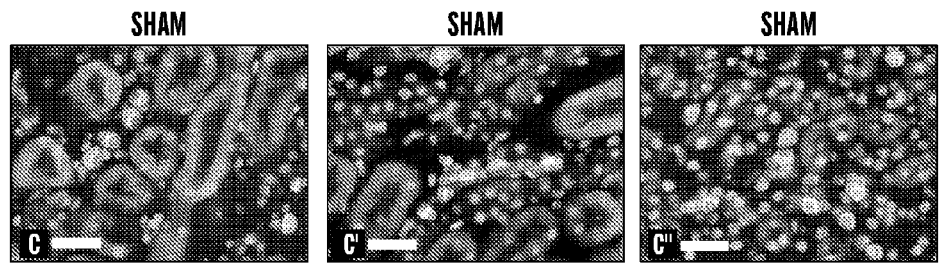
FIG. 11C-11C"
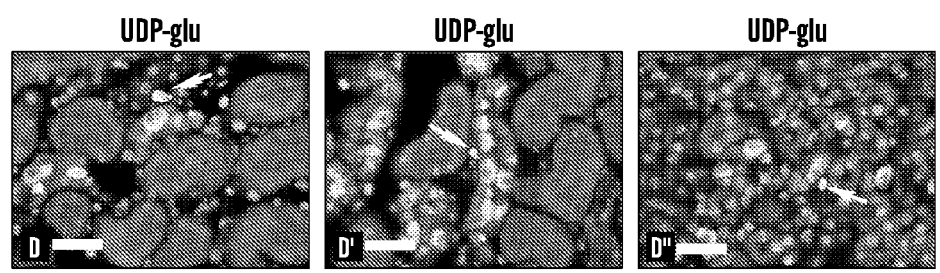
FIG. 11D-11D"

SEQUENCE LISTING

```
<160> NUMBER OF SEQ ID NOS: 115

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agggtctcaa acacccacag                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agctgttcca acccacagag                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttggcccaa ctttgatctc                                                   20

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
cccagagcaa gatgcctatc                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcctcttct gggacatcaa                                                     20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttagggatg gcgctgagta                                                     20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcagctctg tccaagcact                                                     20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccgaggaca acttctctgg                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggggagag caaacactca                                                     20

<210> SEQ ID NO 10
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
caccaaccaa acagcaagtg                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacgatcctg gtccaagtgt                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accaggaact ccaagggttt                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgctttctt cagcagcaat                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctgctctca gttctgacca                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcattttgag ccttctcagg                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 16
ctccctccag ccaaacaata                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagcacaaac catgctgact                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acaagggacc tcctgtcctt                                          20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagaccaaag agcacgaaca                                          20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctggaacag caatggaact                                          20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggcactgag aattttatcc a                                        21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 22
gagcagtccc agtggcttag                                                     20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
taggccctgg aatagcaatg                                                     20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcttggcaaa tggatgtgaa                                                     20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 cagaacccccc atcttctcaa                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 gtggtcccctt cctcttcctt                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaaatgcctg ctgcttgaat                                                     20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 28
tgaagaaatt ccaacaaaac ga                                            22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagccacaga ggcaagagaa                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctggagtaa gggacagcaa                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatgcaaaa tggaagtctg                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggaaagact gggtgtcttc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcacagtcaa ggccgagaat                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gccttctcca tggtggtgaa                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttagcaatgt tcggatgtgc                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggccagccta acagagacag                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acacggcgct ctaaatcagt                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccacccacct acaccaaaag                                                  20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tagaaatgag ggcaggga                                                    18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
```
tggcaaaacc tattccaa                                                      18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgttgtgcga aagaagtgc                                                     20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgagacgaga ccaggagaaa                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggtcaaaaa gtttgccttg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tccaggtcag ttagccttgc                                                    20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccaccacgct cttctgtcta c                                                  21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agggtctggg ccatagaact                                                    20

```
<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caagaaggaa tgggtccaga                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaggcatcac agtccgagtc                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tagccacatc gagggactct                                               20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
accaactggg agggagatg                                                19

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatttcctgc ccctcttctt                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gggagacacg cgtcctataa                                               20
```

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
gtgcccacgt caaggagtat                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ccacttcttc tctgggttgg                                          20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gggcctcaaa ggaaagaatc                                          20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
taccagttgg ggaactctgc                                          20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gtggctaagg accaagacca                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
accacagtga ggaatgtcca                                          20

```
<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttcgctttga cattctcgtg                                                  20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catttgctcc gcatacttga                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acactctcca tcctgctgct                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgagaggaag tcagggggaga                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gactgtcctc tgcgacatca                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttagtggccg atggagtagg                                                  20

<210> SEQ ID NO 65
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccacagtcct catcagagca                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gccagaggtc acctgaacat                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gccagccact tctctttgtc                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caaatcccac tcagccattt                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgggtgtga tcaccttcct                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gaagctggct ttgtctgctc                                              20

<210> SEQ ID NO 71
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cccacattag gatggtggac                                           20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagcctggac aagtctgtga                                           20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcttgtgaag aggcaggaac                                           20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcactggatc cacagtccaa                                           20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgtcaacgtg gcttacaaga                                           20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aatcctcact gctggtggac                                           20

<210> SEQ ID NO 77
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 77
atgtgagctc tggcagcttt                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggaagccaca gtgagtggat                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cttcctgccc ttccatgtta                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggcggaactt cttctgagtg                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcactgcgga tggtttttat                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cagtgtgctt tggacaatgg                                                    20

<210> SEQ ID NO 83
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 83
caagaggcgt aggcaaagtc                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtagggaatg cgtgcaaaat                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ctcattacag ctgccgatca                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tctaaagggc tggcatagga                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gccctcaatg accactttgt                                                    20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tccttggagg ccatgtagac                                                    20

<210> SEQ ID NO 89
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 89
aactccgagc ttccagtcaa                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tctcactcca acgacatcca                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caaatctacc ctccggtcaa                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggttgatgaa gctcctctcg                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cagccttgtc ttcaacgtca                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cttgaggtcg gttcccctat                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 95
tcatcctcac tgtgcctctg                                                    20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctctgaggct cacaccttcc                                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gggctccctc ctctacaact                                                    20

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gcagctccac tgactgtcg                                                     19

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcaattgaac cgcaatccta                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tgcttgtcga gttttttgctc                                                   20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 101
tcatcttctc gaaccccaag                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctggttgtct gtcagctcca                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
caagaaaagc caaacccaaa                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gagggcattt agggaaggtt                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
caagcccggt attatcttcg                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
aggctttcag cttcagatcg                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 107
ctttgagacc agcagcctct                                                20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cagttcagtt ccagatcatc ca                                             22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gctctgcagt caggaaggag                                                20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ggctgagagg atagctgtgg                                                20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cctgtgtgat gaaggatgga                                                20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tatatcctgg ccacctctgg                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
```
ctcggcaaaa tctctgcact                                                20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tggaagcatc catcttttcc                                                20

<210> SEQ ID NO 115
<211> LENGTH: 338
<212> TYPE: PRT
<213> ORGANISM: Homo sapiens

<400> SEQUENCE: 115

Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
            20                  25                  30

Phe Ile Ala Gly Ile Leu Leu Asn Gly Val Ser Gly Trp Ile Phe Phe
        35                  40                  45

Tyr Val Pro Ser Ser Lys Ser Phe Ile Ile Tyr Leu Lys Asn Ile Val
    50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
        115                 120                 125

Thr Ser Phe Ile Gln Ser Val Ser Tyr Ser Lys Leu Leu Ser Val Ile
    130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Leu Ile Val Phe Tyr Thr Ala
        195                 200                 205

Ile Thr Lys Lys Ile Phe Lys Ser His Leu Lys Ser Ser Arg Asn Ser
    210                 215                 220

Thr Ser Val Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270

Leu Arg Tyr Met Lys Glu Phe Thr Leu Leu Leu Ser Ala Ala Asn Val
        275                 280                 285

Cys Leu Asp Pro Ile Ile Tyr Phe Phe Leu Cys Gln Pro Phe Arg Glu

```
            290                 295                 300
Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu
```

COMPOSITIONS AND METHODS FOR DETECTING AND/OR TREATING INFLAMMATION

CROSS-REFERENCE TO RELATED APPLICATION

This application is a 35 U.S.C. § 371 National Phase Entry Application of International Application No. PCT/US2014/064525 filed Nov. 7, 2014, which designates the U.S. and which claims benefit under 35 U.S.C. § 119(e) of U.S. Provisional Application Nos. 61/962,476 filed Nov. 7, 2013, 61/931,146 filed Jan. 24, 2014, and 61/931,184 filed Jan. 24, 2014, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 5, 2015, is named 030258-080682-PCT_SL.txt and is 29,133 bytes in size.

TECHNICAL FIELD

The present invention relates generally to detection and/or treatment for inflammation, particularly renal inflammation.

BACKGROUND

Kidney failure is almost always associated with uncontrolled inflammation. Acute kidney injury (AKI) occurs in two thirds of intensive care unit patients, 40% of patients after cardiac surgery, and 23% of all hospitalized patients. In addition, several factors, including ischemia, nephrotoxins, imaging contrast agents and bacterial endotoxins, contribute to the increased incidence of AKI. AKI contributes to the progression of chronic kidney disease (CKD) to end-stage renal disease. This is accompanied by longer length of stay and, therefore, generates greater costs. High blood pressure and diabetes, which afflict millions of people in the US, are the top two leading causes of CKD. In 2012, 69.53 million cases of CKD were reported in the six major markets (US, France; Germany, Italy, Spain, and UK), with almost 39 million cases in the US alone. It is estimated that the prevalence of CKD will grow by 1.62% annually, reaching 80.83 million cases by 2022. If detected early in its progression, kidney disease can be slowed and the transition to dialysis delayed. However, no early markers of renal inflammation are currently available.

Numerous purinergic receptors are expressed in the kidney, and deregulation of purinergic signaling is associated with several pathologies, including inflammatory renal diseases, hypertension, chronic kidney disease (CKD), acute kidney injury (AKI), diabetic nephropathy and glomerulonephritis (Arulkumaran, N., et al., *Front Physiol*, 2013, 4:194; Burnstock, G., et al., *Purinergic Signal.*, 2014, 10, 71-101). Purinergic receptors are also involved in the regulation of water, electrolyte, and volume homeostasis by collecting duct principal cells (Praetorius, H. A., and Leipziger, J., *Annu Rev Physiol*, 2010, 72:377-393; Rieg, T., and Vallon, V., *Am J Physiol Regul Integr Comp Physiol*, 2009, 296:R419-427; Vallon, V., et al., *Wiley Interdiscip Rev Membr Transp Signal*, 2012, 1:731-742; Kishore, B. K., et al., *Purinergic Signal*, 2009, 5:491-499). However, very little is known on the purinergic regulation of the other major cell type of the collecting duct, the intercalated cell (IC). ICs participate in the maintenance of acid/base homeostasis via the proton-pumping V-ATPase (Breton, S., and Brown, D., *Physiology (Bethesda)*, 2013, 28:318-329; Wagner, C. A., et al., *Physiol. Rev.*, 2004, 84:1263-1314). In the epididymis, ATP and adenosine are potent activators of V-ATPase-dependent proton secretion in clear cells, which are analogous to ICs (Belleannee, C., et al., *Am J Physiol Cell Physiol*, 2010, 298:C817-830). Extracellular ATP stimulates bone resorption in osteoclasts, a process that also requires activity of the V-ATPase (Gallagher, J. A. *J Musculoskelet Neuronal Interact*, 2004, 4:125-127; Kaunitz, J. D., and Yamaguchi, D. T., *J Cell Biochem*, 2008, 105:655-662). These studies suggest a role for the purinergic regulation of acid/base transport in the kidney, but the purinergic receptor signature of ICs still remains to be characterized.

Nucleotide-activated purinergic receptors are separated into two families, P2X receptors that are ligand-gated ion channels, and P2Y receptors that are G protein-coupled receptors (GPCRs) (Praetorius, H. A., and Leipziger, J., *Annu Rev Physiol*, 2010, 72:377-393; Rieg, T., and Vallon, V., *Am J Physiol Regul Integr Comp Physiol*, 2009, 296: R419-427; Vallon, V., et al., *Wiley Interdiscip Rev Membr Transp Signal*, 2012, 1:731-742). While p2y5 was initially proposed to be a nucleotide-receptor, based on its homology to other P2 receptors, it was subsequently shown to be insensitive to nucleotides (Li, Q., et al., *Biochem Biophys Res Commun*, 1997, 236:455-460), but to instead mediate lysophosphatidic acid (LPA) signaling (Lee, C. W., et al., *J Biol Chem*, 2006, 281:23589-23597). Similarly, p2y10 is a lysophospholipid receptor that is not activated by nucleotides (Murakami, M., et al., *Biochem Biophys Res Commun*, 2008, 371:707-712). The $P2Y_{14}$ receptor (also known as GPR105) is the most recent member of the P2Y receptor family (Freeman, K., et al., *Genomics*, 2001, 78:124-128; Chambers, J. K., et al., *J Biol Chem*, 2000, 275:10767-10771).

There is a clear unmet need for novel strategies aimed at detecting early signs of inflammation (before the infiltration of pro-inflammatory immune cells in the damaged tissue) as well as for the treatment of inflammation in the kidney.

SUMMARY

The technology disclosed herein is based, in part, on the discovery that renal intercalated cells can function as sensors, mediators, and effectors of inflammation in the kidney via P2Y14, a receptor that detects the danger molecule UDP-glucose, which is released from injured cells. It was further discovered that the expression of P2Y14 was elevated in mice with renal inflammation. The technology disclosed herein can permit the detection of early stage inflammation.

In one aspect, the technology disclosed herein provides an assay comprising: (i) measuring, in a sample obtained from a subject, a level of P2Y14; (ii) comparing the level of P2Y14 with a reference level; and (iii) identifying the subject as (a) having renal inflammation if the level of P2Y14 is above the reference level; and (b) not having renal inflammation if the level of P2Y14 is at or below the reference level.

In one embodiment, when the level of P2Y14 is above the reference level, the method further comprises providing a treatment appropriate for treating renal inflammation.

In one embodiment, the treatment comprises a P2Y14 inhibitor.

In one embodiment, the level of P2Y14 is a protein level.

In one embodiment, the level of P2Y14 is measured by an immunoassay.

In one embodiment, the sample is contacted with an anti-P2Y14 antibody.

In one embodiment, the anti-P2Y14 antibody is detectably labeled or capable of generating a detectable signal.

In one embodiment, the antibody is fluorescently labeled.

In one embodiment, the level of P2Y14 is measured by measuring a nucleic acid encoding P2Y14.

In one embodiment, the reference level is an average P2Y14 level in a population of healthy subjects.

In one embodiment, the reference level is two standard deviations above an average P2Y14 level in a population of healthy subjects.

In one embodiment, the assay detects early stage inflammation.

In one embodiment, the assay further comprises measuring a level of UDP-glucose in a sample obtained from the subject, and comparing the level of UDP-glucose with a reference level.

In one embodiment, the sample is a urine sample.

In one embodiment, the subject is a mammal.

In one embodiment, the mammal is a human.

In one aspect, the technology disclosed herein provides a method of detecting renal inflammation of a subject, the method comprising: (i) assaying, in a sample obtained from a subject, a level of P2Y14; (ii) comparing the level of P2Y14 with a reference level; and (iii) identifying the subject as (a) having renal inflammation if the level of P2Y14 is above the reference level; and (b) not having renal inflammation if the level of P2Y14 is at or below the reference level.

In one embodiment, when the level of P2Y14 is above the reference level, the method further comprises providing a treatment appropriate for treating renal inflammation.

In one embodiment, the treatment comprises a P2Y14 inhibitor.

In one embodiment, the level of P2Y14 is a protein level.

In one embodiment, the level of P2Y14 is measured by an immunoassay.

In one embodiment, the sample is contacted with an anti-P2Y14 antibody.

In one embodiment, the anti-P2Y14 antibody is detectably labeled or capable of generating a detectable signal.

In one embodiment, the antibody is fluorescently labeled.

In one embodiment, the level of P2Y14 is measured by measuring a nucleic acid encoding P2Y14.

In one embodiment, the reference level is an average P2Y14 level in a population of healthy subjects.

In one embodiment, the reference level is two standard deviations above an average P2Y14 level in a population of healthy subjects.

In one embodiment, the method detects early stage inflammation.

In one embodiment, the method further comprises measuring a level of UDP-glucose in a sample obtained from the subject, and comparing the level of UDP-glucose with a reference level.

In one embodiment, the sample is a urine sample.

In one embodiment, the subject is a mammal.

In one embodiment, the mammal is a human.

In one aspect, the technology disclosed herein provides a method of monitoring treatment progress in a subject suffering from renal inflammation, the method comprising: (i) measuring, at a first time point, a first level of P2Y14 in a first sample obtained from the subject; (ii) administering to the subject a therapeutic agent for treating renal inflammation; and (iii) measuring, at a second time point, a second level of P2Y14 in a second sample obtained from the subject, wherein the second time point is later than the first time point and after said administration, and wherein if the second level is significantly lower than the first level, then the treatment is considered to be effective.

In one embodiment, the first sample and the second sample are urine samples.

In one embodiment, the therapeutic agent is a P2Y14 inhibitor.

In one embodiment, the subject is a human.

In one aspect, the technology disclosed herein provides a method of treating a subject having renal inflammation, the method comprising administering a P2Y14 inhibitor to the subject.

In one embodiment, the P2Y14 inhibitor is PPTN or an anti-P2Y14 antibody.

In one embodiment, the subject is a human.

In one aspect, the technology disclosed herein provides a method of treating a subject determined to have a level of P2Y14 above a reference level, the method comprising administering a treatment appropriate for treating renal inflammation.

In one embodiment, the treatment appropriate for treating renal inflammation comprises a P2Y14 inhibitor.

In one embodiment, the P2Y14 inhibitor is PPTN or an anti-P2Y14 antibody.

In one embodiment, the subject is a human.

In one aspect, the technology disclosed herein provides an assay comprising: (i) measuring, in a sample obtained from a subject, a level of UDP-glucose; (ii) comparing the level of UDP-glucose with a reference level; and (iii) identifying the subject as (a) having renal inflammation if the level of UDP-glucose is above a reference level; and (b) not having renal inflammation if the level of UDP-glucose is at or below the reference level.

In one embodiment, when the level of UDP-glucose is above the reference level, the method further comprises providing a treatment appropriate for treating renal inflammation.

In one embodiment, the treatment comprises a P2Y14 inhibitor.

In one embodiment, the reference level is an average UDP-glucose level in a population of healthy subjects.

In one embodiment, the reference level is two standard deviations above an average UDP-glucose level in a population of healthy subjects.

In one embodiment, the assay detects early stage inflammation.

In one embodiment, the sample is a urine sample.

In one embodiment, the subject is a mammal.

In one embodiment, the mammal is a human.

In one aspect, the technology disclosed herein provides a method of detecting renal inflammation of a subject, the method comprising: (i) assaying, in a sample obtained from a subject, a level of UDP-glucose; (ii) comparing the level of UDP-glucose with a reference level; and (iii) identifying the subject as (a) having renal inflammation if the level of UDP-glucose is above a reference level; and (b) not having renal inflammation if the level of UDP-glucose is at or below the reference level.

In one embodiment, when the level of UDP-glucose is above the reference level, the method further comprises providing a treatment appropriate for treating renal inflammation.

In one embodiment, the treatment comprises a P2Y14 inhibitor.

In one embodiment, the reference level is an average UDP-glucose level in a population of healthy subjects.

In one embodiment, the reference level is two standard deviations above an average UDP-glucose level in a population of healthy subjects.

In one embodiment, the method detects early stage inflammation.

In one embodiment, the sample is a urine sample.

In one embodiment, the subject is a mammal.

In one embodiment, the mammal is a human.

In one aspect, the technology disclosed herein provides a method of monitoring treatment progress in a subject suffering from renal inflammation, the method comprising: (i) measuring, at a first time point, a first level of UDP-glucose in a first sample obtained from the subject; (ii) administering to the subject a therapeutic agent for treating renal inflammation; and (iii) measuring, at a second time point, a second level of UDP-glucose in a second sample obtained from the subject, wherein the second time point is later than the first time point and after said administration, and wherein if the second level is significantly lower than the first level, then the treatment is considered to be effective.

In one embodiment, the first sample and the second sample are urine samples.

In one embodiment, the therapeutic agent is a P2Y14 inhibitor.

In one embodiment, the subject is a human.

In one aspect, the technology disclosed herein provides a method of treating a subject determined to have a level of UDP-glucose above a reference level, the method comprising administering a treatment appropriate for treating renal inflammation.

In one embodiment, the treatment appropriate for treating renal inflammation comprises a P2Y14 inhibitor.

In one embodiment, the P2Y14 inhibitor is PPTN or an anti-P2Y14 antibody.

In one embodiment, the subject is a human.

BRIEF DESCRIPTION OF THE DRAWINGS

FIG. 4A shows representative immunoblot profile of P2Y14 in two EGFP(+) cell samples isolated by FACS.

FIG. 4B shows binding of [3H]UDP-glucose to total membranes prepared from FACS isolated EGFP(+) and EGFP(−) cells in the presence or absence of a saturating concentration ($10^{-5}$ M) of unlabeled UDP-glucose or ATP. Data are represented as fold changes compared to the binding measured in the presence of unlabeled UDP-glucose. Each bar represents the average of 3 independent experiments performed in triplicate. Values are expressed as mean±SEM, * P<0.05.

FIG. 5A is a set of representative immunoblots of pERK (upper lanes) and total ERK (lower lanes) in EGFP(+) cells (left panel) and EGFP(−) cells (right panel).

FIG. 5B is a bar graph showing that densitometry analysis of ERK phosphorylation is represented as % increase of the ratio of pERK/total ERK relative to control. Values (in % of control) are means±SEM (n=3), *P<0.05.

FIG. 6A shows RT-PCR analysis of IC markers including the V-ATPase a4 subunit (V0A4), the V-ATPase B1 subunit (V1B1) and AE1, and the principal cell marker aquaporin 2 (AQP2), as well as $P2Y_{14}$ in MDCK-C11 cells.

FIG. 6B shows representative immunoblots following plasma membrane biotinylation showing cell surface versus total protein expression of the V-ATPase B1 and A subunits, and actin.

FIG. 6C shows RT-PCR detection of P2 receptors in MDCK-C11 cells.

FIG. 6D shows immunoblot profile of $P2Y_{14}$ expression in MDCK-C11. Plasma membrane (left) and total cell expression (right) are represented under control conditions (C) and after treatment with endoglycosydase H (H) and PNGase F (F).

FIG. 6E shows X-Z confocal microscopy representation of MDCK-C11 cells grown on filter, showing $P2Y_{14}$ expression (visualized as red). Plasma membrane is labeled with biotin-streptavidin FITC (visualized as green). The merge panel shows partial co-localization of $P2Y_{14}$ with biotin in the apical membrane (visualized as orange/yellow) as well as sub-apical localization (visualized as red). Scale bars=4 μm.

FIG. 6F shows concentration-dependent inhibition of [$^3$H]UDP-glucose binding to MDCK-C11 membranes by unlabeled ligands. Membranes (15 μg protein) were incubated for 3 hours at 22° C. with [$^3$H]UDP-glucose (3 nM) and increasing concentrations of UDP-glucose or ATP. Each point represents the average of 4 independent experiments performed in triplicate. The data are expressed as values relative to the total binding observed in the absence of unlabeled ligand and are corrected for non specific binding determined in the presence of a saturating concentration of UDP-glucose (10 μM).

FIG. 7A shows representative immunoblots showing triplicates of ERK1/2 phosphorylation (upper lane) versus total ERK1/2 (lower lane) in cells pretreated with vehicle or the P2Y$_{14}$ antagonist PPTN (10 μM), in the absence (CTRL) or presence of 100 μM UDP-glucose (UDP-glu).

FIG. 7B shows quantification of the ratio of p-ERK/total ERK (lower panel) showed that PPTN prevented the increase in ERK1/2 phosphorylation induced by UDP-glu in cells treated with the vehicle only. Values are represented as % of controls as means±SEM (n=3), **p<0.001.

FIGS. 11A-11E are experimental data showing immunolocalization of neutrophils in kidney medulla of mice 48 h after injection with saline (Sham) or 100 tM UDP-glucose.

FIGS. 11A-11B is a set of mosaic, low magnification images of kidney medulla double-labeled for P2Y$_{14}$ (visualized as green) and the neutrophil marker Ly6G (visualized as red; white circles) from mice injected with saline (FIG. 11A) or 100 tM UDP-glucose (FIG. 11B). Scale bars=200 μm.

FIGS. 11C-11D" is a set of high magnification images of the medullary regions showing neutrophil infiltration after UDP-glucose injection (FIGS. 11D, 11D', 11D") but not in the sham animals (FIGS. 11C, 11C', 11C"). Neutrophils (arrows) were often seen in close proximity to ICs, labeled for P2Y$_{14}$ (visualized as green), after UDP-glucose injection. Scale bars=25 μm.

FIG. 11E is a bar graph showing flow cytometry analysis of neutrophil counts (Ly6G positive) from cortex and medulla in control mice (Sham) and after UDP-glucose injection.

DETAILED DESCRIPTION

Figure 1:
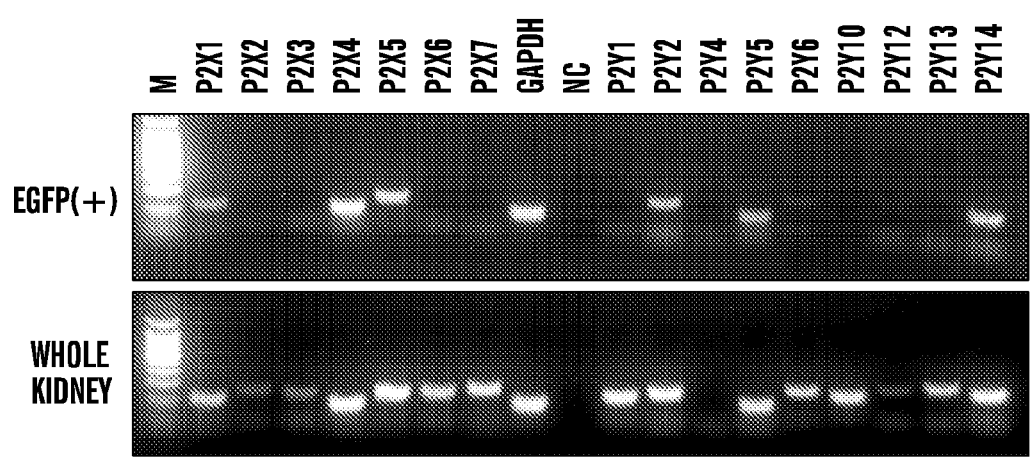
FIG. 1 is experimental data showing RT-PCR detection of P2 receptors in whole kidney (lower panel) and in EGFP(+) cells (upper panel) isolated by fluorescence-activated cell sorting (FACS) from B1-EGFP mouse kidneys. GAPDH was used as positive control. NC=no template control.

The present disclosure is based, in part, on the discovery that P2Y14 and/or UDG-glucose can be used as biomarkers for the detection of renal inflammation. Detection of elevated levels of P2Y14 and/or UDG-glucose in a sample from a subject compared to a reference level can thus be used to indicate the presence of renal inflammation in the subject. Advantageously, early stage inflammation can be detected using one or both of these biomarkers. Accordingly, embodiments of the technology described herein provide, among other things, assays, methods, and systems for determining whether a subject has renal inflammation, methods for monitoring treatment progress in a subject having renal inflammation, and methods for treating a subject having renal inflammation. It should be noted that P2Y14 and UDP-glucose can be used as biomarkers independently or in combination.

The P2Y$_{14}$ receptor (also known as GPR105 or SC-GPR) is the most recent member of the P2Y receptor family (Freeman, K., et al., *Genomics*, 2001, 78:124-128; Chambers, J. K., et al., *J Biol Chem*, 2000, 275:10767-10771). P2Y14 is specifically activated by nucleotide sugars including UDP-glucose and it is insensitive to ADP/ATP and UTP (Chambers, J. K., et al., *J Biol Chem*, 2000, 275:10767-10771). Most nucleotides are rapidly degraded after their release, but UDP-glucose resists hydrolysis by ectonucleotidases (Zimmermann, H., *Naunyn Schmiedebergs Arch Pharmacol*, 2000, 362:299-309). While virtually all cells release nucleotides under basal conditions (Lazarowski, E. R., et al., *Mol Pharmacol*, 2003, 63:1190-1197), this release can be accentuated in response to stimuli leading to activation of purinergic receptors (Leipziger, J., *Curr Opin Nephrol Hypertens*, 2011, 20:518-522). UDP-glucose, extracellular ATP and adenosine are emerging as immune-regulatory factors known as DAMPs (damage associated molecular pattern) molecules (Chen, Y., et al., *Science*, 2006, 314:1792-1795; Elliott, M. R., et al., *Nature*, 2009, 461:282-286). DAMPs initiate sterile inflammatory reactions, as opposed to PAMP (pathogen associated molecular patterns), which perpetuate infectious pro-inflammatory responses (Elliott, M. R., et al., *Nature*, 2009, 461:282-286; Harden, T. K., et al., *Acta Physiol (Oxf)*, 2010, 199:149-160; Chen, G. Y., and Nunez, G. Nat Rev Immunol, 2010, 10:826-837; Kono, H., and Rock, K. L., *Nat Rev Immunol*, 2008, 8:279-289).

As used herein, the term "P2Y14" generally refers to a P2Y14 polypeptide or a P2Y14 polynucleotide that is similar or identical to the sequence of a wild-type P2Y14.

The wild-type P2Y14 sequences of various species are available on the world wide web such as the NCBI. For example, human P2Y14 amino acid sequence is included herein as (SEQ ID NO: 115) for reference:
P2Y purinoceptor 14 (P2Y14) [*Homo sapiens*] (NCBI Reference Sequence: NP_001074924.1):
1 minststqpp descsqnlli tqqiipvlyc mvfiagilln gvsgwiffyv pssksfiiyl
61 kniviadfvm sltfpfkilg dsglgpwqln vfvcrvsavl fyvnmyvsiv ffglisfdry
121 ykivkplwts fiqsysyskl lsvivwmlml llavpniilt nqsvrevtqi kcielkselg 181 rkwhkasnyi fvaifwivfl llivfytait kkifkshlks srnstsvkkk ssrnifsivf
241 vffvcfvpyh iaripytksq teahyscqsk eilrymkeft lllsaanvcl dpiiyfflcq
301 pfreilckkl hiplkaqndl disrikrgnt tlestdtl (SEQ ID NO: 115)

In one aspect, the technology disclosed herein provides a method of detecting renal inflammation of a subject, the method comprising: (i) assaying, in a sample obtained from a subject, a level of P2Y14; (ii) comparing the level of P2Y14 with a reference level; and (iii) identifying the subject as (a) having renal inflammation if the level of P2Y14 is above the reference level; and (b) not having renal inflammation if the level of P2Y14 is at or below the reference level.

In various aspects described herein, methods for measuring P2Y14 or a fragment thereof from a sample are known in the art, including, but not limited to measuring mRNA expression using PCR or real-time PCR, protein analysis using western blot, immunoassay, and/or sequencing analysis. Thus, in some embodiments, nucleic acid molecules from a patient's sample can be isolated or assayed to measure P2Y14 mRNA expression, or proteins can be isolated or assayed to measure P2Y14 protein expression.

P2Y14 protein or polypeptide levels can be measured using a variety of methods known in the art including, but not limited to, an immunological test, surface plasmon resonance, and photonic crystal-based detection. Immunological tests include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments, the immunoassay can be a quantitative or a semi-quantitative immunoassay.

An immunoassay is a biochemical test that measures the concentration of a substance in a biological sample, typically a fluid sample, using the interaction of an antibody or antibodies to its antigen. The assay takes advantage of the highly specific binding of an antibody with its antigen. In some embodiments, specific binding of the P2Y14 molecule with an anti-P2Y14 antibody forms a P2Y14-antibody complex. The complex can then be detected by a variety of methods known in the art. An immunoassay also often involves the use of a detection antibody. Anti-P2Y14 antibodies are commercially available through vendors such as Alomone Labs (Jerusalem, Israel), Sigma Aldrich, and Merck Millipore. In one embodiment, the anti-P2Y14 antibody is detectably labeled or capable of generating a detectable signal. In one embodiment, the anti-P2Y14 antibody is fluorescently labeled.

In some embodiments, P2Y14 levels are measured by ELISA, also called enzyme immunoassay or EIA. ELISA is a biochemical technique that detects the presence of an antibody or an antigen in a sample.

In one embodiment, an ELISA involving at least one antibody with specificity for the particular desired antigen (i.e. P2Y14) can be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In one embodiment, a sandwich ELISA is used, where two types of anti-P2Y14 antibodies can be used. There are other different forms of ELISA, which are well known to those skilled in the art. Standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference for their teachings on ELISA.

In one embodiment, the levels of P2Y14 in a sample can be detected by a lateral flow immunoassay test (LFIA), also known as the immunochromatographic assay, or strip test. LFIAs are a simple device intended to detect the presence (or absence) of antigen, e.g. P2Y14, in a fluid sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of P2Y14 present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

A typical test strip consists of the following components: (1) sample application area comprising an absorbent pad (i.e., the matrix or material) onto which the test sample is applied; (2) conjugate or reagent pad—this contains antibody reagent(s) specific to the target antigen (e.g. specific P2Y14 or fragment thereof) which can be conjugated to colored particles (e.g., colloidal gold particles, or latex microspheres); (3) test results area comprising a reaction membrane—typically a hydrophobic nitrocellulose or cellulose acetate membrane onto which antibody reagents (e.g., anti-P2Y14 antibodies) are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of P2Y14 using antibody reagents as described herein.

A urine dipstick is a colorimetric chemical assay. It consists of a reagent stick-pad, which is immersed in a fresh urine specimen and then withdrawn. After predetermined times the colors of the reagent pad are compared to standardized reference charts. The urine dipstick offers an inexpensive and fast method to perform screening urinalyses, which help in identifying the presence of various diseases or health problems. A urine dipstick provides a simple and clear diagnostic guideline and can be used in the methods and kits as described herein. Accordingly, one aspect of the present technology relates to a method for detecting P2Y14 using a device, such as a dipstick, as described herein.

Other techniques can be used to detect the level of P2Y14 in a sample. One such technique is the dot blot, and adaptation of Western blotting (Towbin et at., Proc. Nat. Acad. Sci. 76:4350 (1979)). In a Western blot, P2Y14 can be dissociated with detergents and heat, and separated on an SDS-PAGE gel before being transferred to a solid support, such as a nitrocellulose or PVDF membrane. The membrane is incubated with an antibody reagent specific for P2Y14. The membrane is then washed to remove unbound proteins and proteins with non-specific binding. Detectably labeled enzyme-linked secondary or detection antibodies can then be used to detect and assess the amount of P2Y14 in the sample tested. The intensity of the signal from the detectable label corresponds to the amount of enzyme present, and therefore the amount of P2Y14. Levels can be quantified, for example by densitometry.

The level of P2Y14 can also be measured by measuring the biological activity of P2Y14, such as the downstream signaling activity of P2Y14, or the UDP-glucose binding activity.

In some embodiments, the level of P2Y14 can also be measured by measuring the level of mRNA encoding P2Y14. Methods of measuring mRNA levels include, but are not limited to, polymerase chain reaction (PCR, e.g., quantitative or semi-quantitative, or reverse transcription-PCR), hybridization assay, Northern blotting, primer extension, ribonuclease protection, and variations of these.

Injured cells release UDP-glucose, a damage-associated molecular pattern molecule (DAMP) that signals through the purinergic receptor P2Y14 to initiate the release of pro-inflammatory chemokines (PIC). And thus UDP-glucose level can also be used as an indicator for inflammation. In one aspect, the technology disclosed herein provides a method of detecting renal inflammation of a subject, the method comprising: (i) assaying, in a sample obtained from a subject, a level of UDP-glucose; (ii) comparing the level of UDP-glucose with a reference level; and (iii) identifying the subject as (a) having renal inflammation if the level of UDP-glucose is above a reference level; and (b) not having renal inflammation if the level of UDP-glucose is at or below the reference level.

UDP-glucose levels can be measured using a variety of methods known in the art, such as HPLC. In some embodiments, UDP-glucose levels can be measured using the protocols described in Barrett et al., Molec. Pharmacol., 2013, 84, 41-49, the contents of which are incorporated herein by reference in their entirety.

P2Y14 and/or UDP-glucose can be used for monitoring the treatment progress in a subject having renal inflammation. For example, by measuring the levels of P2Y14 and/or UDP-glucose at multiple time points during the treatment, a decrease in the levels of P2Y14 and/or UDP-glucose over time can indicate that the treatment is effective. In one aspect, the technology disclosed herein provides a method of monitoring treatment progress in a subject suffering from renal inflammation, the method comprising: (i) measuring, at a first time point, a first level of P2Y14 or UDP-glucose in a first sample obtained from the subject; (ii) administering to the subject a therapeutic agent for treating renal inflammation; and (iii) measuring, at a second time point, a second level of P2Y14 or UDP-glucose in a second sample obtained from the subject, wherein the second time point is later than the first time point and after said administration, and wherein if the second level is significantly lower than the first level, then the treatment is considered to be effective.

Sample

The terms "sample", "biological sample", or "test sample" as used herein denote a sample taken or isolated from a biological organism, e.g., an animal or human. Exemplary biological samples include, but are not limited to, a biofluid sample; a body fluid sample, blood (including whole blood); serum; plasma; urine; saliva; a biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, the sample used for the assays and methods described herein can comprise a urine sample collected from a subject to be tested. In some embodiments, the sample used for the assays and methods described herein can comprise a blood sample collected from a subject to be tested.

The test sample can be obtained by removing a sample from a subject, but can also be accomplished by using previously isolated samples (e.g. isolated at a prior time point and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample.

Reference Level

In some embodiments, the reference level can correspond to an average level of P2Y14 or UDP-glucose in a sample (e.g., urine) of a normal healthy subject or a population of normal healthy subjects. This would be a "normal" level. As used herein, the term "normal healthy subject" refers to a subject who has no symptoms of any diseases or disorders, or who is not identified with any diseases or disorders, or who is not on any medication treatment, or a subject who is identified as healthy by physicians based on medical examinations. It should be noted and obvious to a skilled artisan that one should only compare the measured P2Y14 level with the reference level of P2Y14, and the measured UDP-glucose level with the reference level of UDP-glucose.

In some embodiments, the reference level can be at least one standard deviation (including, e.g., at least two standard deviations) above the average level of P2Y14 or UDP-glucose in a sample (e.g., urine) of a normal healthy subject or a population of normal healthy subjects. In some embodiments, the reference level can be at least two standard deviations above the average level of P2Y14 or UDP-glucose in a sample (e.g., urine) of a normal healthy subject or a population of normal healthy subjects. In these embodiments, any level above the reference level is considered to be significantly different from the average level of P2Y14 or UDP-glucose in a sample of a normal healthy subject or a population of normal healthy subjects.

In some embodiments, the reference level can be a level of P2Y14 or UDP-glucose in a control sample, a pooled sample of control individuals, or a numeric value or range of values based on the same. It is also contemplated that a set of standards can be established with reference levels providing thresholds indicative of the severity of renal inflammation.

In some embodiments, the reference level can be an average level of P2Y14 or UDP-glucose in a sample (e.g., urine) of subject or a population of subjects without inflammation, or more specifically, renal inflammation. These subjects might have a disease other than renal inflammation. In some embodiments, the reference level can be at least one standard deviation (including, e.g., at least two standard deviations) above the average level of P2Y14 or UDP-glucose in a sample (e.g., urine) of a subject or a population of subjects without inflammation, or more specifically, renal inflammation.

In some embodiments, the reference level can be a level of P2Y14 or UDP-glucose in a sample (e.g., urine) of the same subject measured at an earlier time point, e.g., before or during the treatment. In these embodiments, a physician monitors the subject's P2Y14 or UDP-glucose levels over time for, e.g., determining treatment efficacy or managing the disease progression.

In some embodiments, the level of P2Y14 measured in a sample from a subject identified as having renal inflammation can be at least 5%, at least 10%, at least 20%, at least 30%, at least 40%, at least 50%, at least 60%, at least 70%, at least 80%, at least 90%, at least 100%, at least 150%, at least 200%, or at least 300% higher than the reference level.

In some embodiments, the level of UDP-glucose measured in a sample from a subject identified as having renal inflammation can be at least 5%, at least 10%, at least 20%, at least 30%, at least 40%, at least 50%, at least 60%, at least 70%, at least 80%, at least 90%, at least 100%, at least 150%, at least 200%, or at least 300% higher than the reference level.

It should be noted that the reference level can be different, depending on factors such as the sample type from which the reference level is derived, gender, age, weight, and ethnicity. Thus, reference levels accounting for these and other variables can provide added accuracy for the methods described herein.

Computer Systems

In some embodiments of the assays and/or methods described herein, the assay/method comprises or consists essentially of a system for determining (e.g. transforming and measuring) the level of P2Y14 and/or UDP-glucose as described herein and comparing it to a reference level. If the comparison system, which can be a computer implemented system, indicates that the amount of the measured level of P2Y14 and/or UDP-glucose is statistically higher than that of the reference amount, the subject from which the sample is collected can be identified as having renal inflammation.

In one embodiment, provided herein is a system comprising: (a) at least one memory containing at least one computer program adapted to control the operation of the computer system to implement a method that includes (i) a determination module configured to measure the level of P2Y14 and/or UDP-glucose in a test sample obtained from a subject; (ii) a storage module configured to store output data from the determination module; (iii) a computing module adapted to identify from the output data whether the measured level of P2Y14 and/or UDP-glucose in the test sample obtained from the subject is higher, by a statistically significant amount, than a reference level, and to provide a retrieved content; (iv) a display module for displaying for retrieved content (e.g., the amount of the measured level of P2Y14 and/or UDP-glucose, or whether the measured level of P2Y14 and/or UDP-glucose is higher than the reference level); and (b) at least one processor for executing the computer program.

Embodiments can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the technology discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the technology described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments can include at minimum a determination module, a storage module, a computing module, and a display module. The functional modules can be executed on one, or multiple, computers, or by using one, or multiple, computer networks. The determination module has computer executable instructions to provide e.g., levels of expression products etc in computer readable form.

The determination module can comprise any system for detecting a signal resulting from the detection of P2Y14 and/or UDP-glucose in a biological sample. In some embodiments, such systems can include an instrument, e.g., a plate reader for measuring absorbance. In some embodiments, such systems can include an instrument, e.g., the Cell Biosciences NANOPRO 1000™ System (Protein Simple; Santa Clara, Calif.) for quantitative measurement of proteins.

The information determined in the determination system can be read by the storage module. As used herein the "storage module" is intended to include any suitable computing or processing apparatus or other device configured or adapted for storing data or information. Examples of electronic apparatus suitable for use with the technology described herein include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, patient name, and numerical value of the level of P2Y14 and/or UDP-glucose. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment of any of the systems described herein, the storage module stores the output data from the determination module. In additional embodiments, the storage module stores the reference information such as levels of P2Y14 and/or UDP-glucose in healthy subjects. In some embodiments, the storage module stores the information such as levels of P2Y14 and/or UDP-glucose measured from the same subject in earlier time points.

The "computing module" can use a variety of available software programs and formats for computing the levels of P2Y14 and/or UDP-glucose. Such algorithms are well established in the art. A skilled artisan is readily able to determine the appropriate algorithms based on the size and quality of the sample and type of data. The data analysis can be implemented in the computing module. In one embodiment, the computing module further comprises a comparison module, which compares the level of P2Y14 and/or UDP-glucose in the test sample obtained from a subject as described herein with the reference level. By way of example, when the level of P2Y14 and/or UDP-glucose in the test sample obtained from a subject is measured, a comparison module can compare or match the output data, e.g. with the reference level. In certain embodiments, the reference level has been pre-stored in the storage module. During the comparison or matching process, the comparison module can determine whether the level of P2Y14 and/or UDP-glucose in the test sample obtained from a subject is higher than the reference level to a statistically significant degree. In various embodiments, the comparison module can be configured using existing commercially-available or freely-available software for comparison purpose, and may be optimized for particular data comparisons that are conducted.

The computing and/or comparison module, or any other module, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware, as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment, users can directly access data (via Hypertext links for example) residing on Internet databases using a HTML interface provided by Web browsers and Web servers.

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the relative levels of P2Y14 and/or UDP-glucose in the test sample obtained from a subject as compared to a reference level. In certain embodiments, the content displayed on the display module can indicate whether the levels of P2Y14 and/or UDP-glucose are found to be statistically significantly higher in the test sample obtained from a subject as compared to a reference level. In some embodiments, the content displayed on the display module can show the levels of P2Y14 and/or UDP-glucose from the subject measured at multiple time points, e.g., in the form of a graph. In some embodiments, the content displayed on the display module can indicate whether the subject has renal inflammation. In certain embodiments, the content displayed on the display module can indicate whether the subject is in need of a treatment for renal inflammation.

In one embodiment, the content based on the computing and/or comparison result is displayed on a computer monitor. In one embodiment, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the technology relating to determining the levels of P2Y14 and/or UDP-glucose, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Devices/Kits

Provided herein are kits and devices for practicing the assays and methods described herein.

In some embodiments, described herein is a device for measuring the P2Y14 level in a test sample from a subject, the device comprising: (a) a P2Y14-specific antibody or antigen-binding portion thereof; and (b) at least one solid support, wherein the antibody or antigen-binding portion thereof of part (a) are deposited on the support. In some embodiments, the device can perform an assay in which an antibody-protein or antibody-peptide complex is formed. In some embodiments, the solid support can be in the format of a dipstick, a microfluidic chip, a multi-well plate or a cartridge. The kits or devices can employ immuno-based lateral flow technology to produce a signal.

In some embodiments, described herein is a kit comprising: a device as described in the preceding paragraph; and at least a detection antibody. In some embodiments, the detection antibody can be specific for P2Y14. In some embodiments, the detection antibody can be detectably labeled. In some embodiments, the kit can further comprise at least an agent for producing a detectable signal from the detection antibody.

In some embodiments, the kit or device can comprise a reference, e.g. a reference sample or reference signal. In some embodiments, the reference sample can comprise a urine sample from a healthy subject.

Methods of Treatment

In some embodiments, when the subject is identified as having renal inflammation, the assay or method further comprises administering to the subject a treatment appropriate for treating renal inflammation. Renal inflammation, also called nephritis, can include several types such as glomerulonephritis, membranoproliferative glomerulonephritis, interstitial nephritis, IgA nephropathy, pyelonephritis, autoimmune disorders related to CKD and inflammation, lupus nephritis, Goodpasture's syndrome, and Wegener's granulomatosis.

P2Y14 can be targeted for the treatment of renal inflammation. Accordingly, in some embodiments, the treatment appropriate for treating renal inflammation comprises a P2Y14 inhibitor.

In some embodiments, the P2Y14 inhibitor is a small or large organic or inorganic molecule. As used herein, the term "small molecule" refers to natural or synthetic molecules having a molecular mass of less than about 5 kD, organic or inorganic compounds having a molecular mass of less than about 5 kD, less than about 2 kD, or less than about 1 kD. In one embodiment, the P2Y14 inhibitor is a 4,7-disubstituted naphthoic acid derivative. In one embodiment, the P2Y14 inhibitor is PPTN, i.e., 4-[4-(piperidin-4-yl)phenyl]-7-[4-(trifluoromethyl)phenyl]-2-naphthoic acid. Details about PPTN as a P2Y14 inhibitor can be found in Gauthier J Y, et al., Bioorg Med Chem Lett., 2011, 21:2836-2839, the contents of which are incorporated herein by reference in their entirety. In one embodiment, the P2Y14 inhibitor is Prodrug 7j hydrochloride, which can be available, e.g., from Axon Medchem.

In some embodiments, the P2Y14 inhibitor can be an anti-P2Y14 antibody molecule or an antigen-binding fragment thereof. Suitable antibodies include, but are not limited to, polyclonal, monoclonal, chimeric, humanized, recombinant, single chain, $F_{ab}$, $F_{ab'}$, $F_{sc}$, $R_v$, and $F_{(ab')2}$ fragments. In some embodiments, neutralizing antibodies can be used as inhibitors of P2Y14. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The extracellular domain of the P2Y14 polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues.

Useful monoclonal antibodies and fragments can be derived from any species (including humans) or can be formed as chimeric proteins which employ sequences from more than one species. Human monoclonal antibodies or "humanized" murine antibody can also be used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction in the possibility of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

In some embodiments, the P2Y14 inhibitor is a nucleic acid or a nucleic acid analog or derivative thereof, also referred to as a nucleic acid agent herein. In the context of this disclosure, the term "nucleic acid" refers to a polymer or oligomer of nucleotide or nucleoside monomers consisting of naturally occurring bases, sugars and intersugar linkages. The term "nucleic acid" or "oligonucleotide" or "polynucleotide" are used interchangeably herein and can mean at least two nucleotides covalently linked together. As will be appreciated by those skilled in the art, the depiction of a single strand also defines the sequence of the complementary strand. Thus, a nucleic acid also encompasses the complementary strand of a depicted single strand.

Without limitation, the nucleic acid agent can be single-stranded or double-stranded. A single-stranded nucleic acid agent can have double-stranded regions, e.g., where there is internal self-complementarity, and a double-stranded nucleic acid agent can have single-stranded regions. The nucleic acid can be of any desired length. In particular embodiments, nucleic acid can range from about 10 to 100 nucleotides in length. In various related embodiments, nucleic acid agents, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In some embodiments, nucleic acid agent is from about 9 to about 39 nucleotides in length. In some other embodiments, nucleic acid agent is at least 30 nucleotides in length.

The nucleic acid agent can comprise modified nucleosides as known in the art. Modifications can alter, for example, the stability, solubility, or interaction of the nucleic acid agent with cellular or extracellular components that modify activity. In certain instances, it can be desirable to modify one or both strands of a double-stranded nucleic acid agent. In some cases, the two strands will include different modifications. In other instances, multiple different modifications can be included on each of the strands. The various modifications on a given strand can differ from each other, and can also differ from the various modifications on other strands. For example, one strand can have a modification, and a different strand can have a different modification. In other cases, one strand can have two or more different modifications, and the another strand can include a modification that differs from the at least two modifications on the first strand.

Single-stranded and double-stranded nucleic acid agents that are effective in inducing RNA interference are referred to as siRNA, RNAi agents, iRNA agents, or RNAi inhibitors herein. As used herein, the term "iRNA agent" refers to a nucleic acid agent which can mediate the targeted cleavage of an RNA transcript via an RNA-induced silencing complex (RISC) pathway.

In some embodiments, the P2Y14 inhibitor is an antisense oligonucleotide. One of skill in the art is well aware that single-stranded oligonucleotides can hybridize to a complementary target sequence and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA. Alternatively, or in addition to, the single-stranded oligonucleotide can modulate the expression of a target sequence via RISC mediated cleavage of the target sequence, i.e., the single-stranded oligonucleotide acts as a single-stranded RNAi agent. A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure.

In general, any method of delivering a nucleic acid molecule can be adapted for use with the nucleic acid agents described herein.

In some embodiments, the P2Y14 inhibitor can also be a peptide, a peptidomimetic, a protein, a monosaccharide, a disaccharide, a trisaccharide, an oligosaccharide, a polysaccharide, a lipid, a glycosaminoglycan, an extract made from a biological material, or any combinations thereof.

The data obtained from cell culture assays and animal studies can be used in formulating a range of dosages of P2Y14 inhibitors for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The term "effective amount" as used herein refers to the amount of a therapy needed to alleviate at least one or more symptoms of the disease or disorder (e.g., inflammation or renal inflammation), and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In some embodiments, an effective amount of a P2Y14 inhibitor can be an amount which causes the level of P2Y14 expression to decrease or, at least, to increase at a lower rate than it would be expected to increase in a subject not receiving the P2Y14 inhibitor. In some embodiments, an effective amount can be an amount that decreases the amount of P2Y14 polypeptide present in the subject and/or P2Y14 polypeptide present in a sample (e.g., urine) obtained from a subject by a statistically significant amount.

In some embodiments, an effective amount of a P2Y14 inhibitor can be an amount which reduces the extent of renal inflammation.

In some embodiments, an effective amount of a P2Y14 inhibitor can be an amount that decreases the expression or level of pro-inflammatory chemokines in ICs.

The dosage can be determined by one of skill in the art and can also be adjusted by the individual physician in the event of any complication. Typically, the dosage of a composition comprising a P2Y14 inhibitor disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the P2Y14 inhibitors described herein can improve renal function. For example, renal function is improved by at least 10%, at least 20%, at least 30%, at least 40%, at least 50%, at least 60%, at least 70%, at least 80%, at least 90%, at least 100%, at least 200%, or at least 300%. Measurable markers of renal function, are well known in the medical and veterinary literature and to those of skill in the art, and include, but are not limited to, blood urea nitrogen or "BUN" levels (both static measurements and measurements of rates of increase or decrease in BUN levels), serum creatinine levels (both static measurements and measurements of rates of increase or decrease in serum creatinine levels), measurements of the BUN/creatinine ratio (static measurements of measurements of the rate of change of the BUN/creatinine ratio), urine/plasma ratios for creatinine, urine/plasma ratios for urea, glomerular filtration rates (GFR), serum concentrations of sodium ($Na^+$), urine osmolarity, daily urine output, and the like. Of the above, measurements of the plasma concentrations of creatinine and/or urea or BUN are particularly important and useful readouts of renal function.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

paragraph 1. An assay comprising:
(i) measuring, in a sample obtained from a subject, a level of P2Y14;
(ii) comparing the level of P2Y14 with a reference level; and
(iii) identifying the subject as (a) having renal inflammation if the level of P2Y14 is above the reference level; and (b) not having renal inflammation if the level of P2Y14 is at or below the reference level.

paragraph 2. The assay of paragraph 1, wherein when the level of P2Y14 is above the reference level, the method further comprises providing a treatment appropriate for treating renal inflammation.

paragraph 3. The assay of paragraph 2, wherein the treatment comprises a P2Y14 inhibitor.

paragraph 4. The assay of any one of the preceding paragraphs, wherein the level of P2Y14 is a protein level.

paragraph 5. The assay of paragraph 4, wherein the level of P2Y14 is measured by an immunoassay.

paragraph 6. The assay of paragraph 5, wherein the sample is contacted with an anti-P2Y14 antibody.

paragraph 7. The assay of paragraph 6, wherein the anti-P2Y14 antibody is detectably labeled or capable of generating a detectable signal.

paragraph 8. The assay of paragraph 6 or 7, wherein the antibody is fluorescently labeled.

paragraph 9. The assay of any one of paragraphs 1-3, wherein the level of P2Y14 is measured by measuring a nucleic acid encoding P2Y14.

paragraph 10. The assay of any one of the preceding paragraphs, wherein the reference level is an average P2Y14 level in a population of healthy subjects.

paragraph 11. The assay of any one of paragraphs 1-9, wherein the reference level is two standard deviations above an average P2Y14 level in a population of healthy subjects.

paragraph 12. The assay of any one of the preceding paragraphs, wherein the assay detects early stage inflammation.

paragraph 13. The assay of any one of the preceding paragraphs, further comprising measuring a level of UDP-glucose in a sample obtained from the subject, and comparing the level of UDP-glucose with a reference level.

paragraph 14. The assay of any one of the preceding paragraphs, wherein the sample is a urine sample.

paragraph 15. The assay of any one of the preceding paragraphs, wherein the subject is a mammal.

paragraph 16. The assay of paragraph 15, wherein the mammal is a human.

paragraph 17. A method of detecting renal inflammation of a subject, the method comprising
(i) assaying, in a sample obtained from a subject, a level of P2Y14;
(ii) comparing the level of P2Y14 with a reference level; and
(iii) identifying the subject as (a) having renal inflammation if the level of P2Y14 is above the reference level; and (b) not having renal inflammation if the level of P2Y14 is at or below the reference level.

paragraph 18. The method of paragraph 17, wherein when the level of P2Y14 is above the reference level, the method further comprises providing a treatment appropriate for treating renal inflammation.

paragraph 19. The method of paragraph 18, wherein the treatment comprises a P2Y14 inhibitor.

paragraph 20. The method of any one of paragraphs 17-19, wherein the level of P2Y14 is a protein level.

paragraph 21. The method of paragraph 20, wherein the level of P2Y14 is measured by an immunoassay.

paragraph 22. The method of paragraph 21, wherein the sample is contacted with an anti-P2Y14 antibody.

paragraph 23. The method of paragraph 22, wherein the anti-P2Y14 antibody is detectably labeled or capable of generating a detectable signal.

paragraph 24. The method of paragraph 22 or 23, wherein the antibody is fluorescently labeled.

paragraph 25. The method of any one of paragraphs 17-19, wherein the level of P2Y14 is measured by measuring a nucleic acid encoding P2Y14.

paragraph 26. The method of any one of paragraphs 17-25, wherein the reference level is an average P2Y14 level in a population of healthy subjects.

paragraph 27. The method of any one of paragraphs 17-25, wherein the reference level is two standard deviations above an average P2Y14 level in a population of healthy subjects.

paragraph 28. The method of any one of paragraphs 17-27, wherein the method detects early stage inflammation.

paragraph 29. The method of any one of paragraphs 17-28, further comprising measuring a level of UDP-glucose in a sample obtained from the subject, and comparing the level of UDP-glucose with a reference level.

paragraph 30. The method of any one of paragraphs 17-29, wherein the sample is a urine sample.

paragraph 31. The method of any one of paragraphs 17-30, wherein the subject is a mammal.

paragraph 32. The method of paragraph 31, wherein the mammal is a human.
paragraph 33. A method of monitoring treatment progress in a subject suffering from renal inflammation, the method comprising:
(i) measuring, at a first time point, a first level of P2Y14 in a first sample obtained from the subject;
(ii) administering to the subject a therapeutic agent for treating renal inflammation; and
(iii) measuring, at a second time point, a second level of P2Y14 in a second sample obtained from the subject, wherein the second time point is later than the first time point and after said administration, and wherein if the second level is significantly lower than the first level, then the treatment is considered to be effective.
paragraph 34. The method of paragraph 33, wherein the first sample and the second sample are urine samples.
paragraph 35. The method of paragraph 33 or 34, wherein the therapeutic agent is a P2Y14 inhibitor.
paragraph 36. The method of any one of paragraphs 33-35, wherein the subject is a human.
paragraph 37. A method of treating a subject having renal inflammation, the method comprising administering a P2Y14 inhibitor to the subject.
paragraph 38. The method of paragraph 37, wherein the P2Y14 inhibitor is PPTN or an anti-P2Y14 antibody.
paragraph 39. The method of paragraph 37 or 38, wherein the subject is a human.
paragraph 40. A method of treating a subject determined to have a level of P2Y14 above a reference level, the method comprising administering a treatment appropriate for treating renal inflammation.
paragraph 41. The method of paragraph 40, wherein the treatment appropriate for treating renal inflammation comprises a P2Y14 inhibitor.
paragraph 42. The method of paragraph 41, wherein the P2Y14 inhibitor is PPTN or an anti-P2Y14 antibody.
paragraph 43. The method of any one of paragraphs 40-42, wherein the subject is a human.
paragraph 44. An assay comprising:
(i) measuring, in a sample obtained from a subject, a level of UDP-glucose;
(ii) comparing the level of UDP-glucose with a reference level; and
(iii) identifying the subject as (a) having renal inflammation if the level of UDP-glucose is above the reference level; and (b) not having renal inflammation if the level of UDP-glucose is at or below the reference level.
paragraph 45. The assay of paragraph 44, wherein when the level of UDP-glucose is above the reference level, the method further comprises providing a treatment appropriate for treating renal inflammation.
paragraph 46. The assay of paragraph 45, wherein the treatment comprises a P2Y14 inhibitor.
paragraph 47. The assay of any one of paragraphs 44-46, wherein the reference level is an average UDP-glucose level in a population of healthy subjects.
paragraph 48. The assay of any one of paragraphs 44-46, wherein the reference level is two standard deviations above an average UDP-glucose level in a population of healthy subjects.
paragraph 49. The assay of any one of paragraphs 44-48, wherein the assay detects early stage inflammation.
paragraph 50. The assay of any one of paragraphs 44-49, wherein the sample is a urine sample.
paragraph 51. The assay of any one of paragraphs 44-50, wherein the subject is a mammal.
paragraph 52. The assay of paragraph 51, wherein the mammal is a human.
paragraph 53. A method of detecting renal inflammation of a subject, the method comprising
(i) assaying, in a sample obtained from a subject, a level of UDP-glucose;
(ii) comparing the level of UDP-glucose with a reference level; and
(iii) identifying the subject as (a) having renal inflammation if the level of UDP-glucose is above the reference level; and (b) not having renal inflammation if the level of UDP-glucose is at or below the reference level.
paragraph 54. The method of paragraph 53, wherein when the level of UDP-glucose is above the reference level, the method further comprises providing a treatment appropriate for treating renal inflammation.
paragraph 55. The method of paragraph 54, wherein the treatment comprises a P2Y14 inhibitor.
paragraph 56. The method of any one of paragraphs 53-55, wherein the reference level is an average UDP-glucose level in a population of healthy subjects.
paragraph 57. The method of any one of paragraphs 53-55, wherein the reference level is two standard deviations above an average UDP-glucose level in a population of healthy subjects.
paragraph 58. The method of any one of paragraphs 53-57, wherein the method detects early stage inflammation.
paragraph 59. The method of any one of paragraphs 53-58, wherein the sample is a urine sample.
paragraph 60. The method of any one of paragraphs 53-59, wherein the subject is a mammal.
paragraph 61. The method of paragraph 60, wherein the mammal is a human.
paragraph 62. A method of monitoring treatment progress in a subject suffering from renal inflammation, the method comprising:
(i) measuring, at a first time point, a first level of UDP-glucose in a first sample obtained from the subject;
(ii) administering to the subject a therapeutic agent for treating renal inflammation; and
(iii) measuring, at a second time point, a second level of UDP-glucose in a second sample obtained from the subject, wherein the second time point is later than the first time point and after said administration, and wherein if the second level is significantly lower than the first level, then the treatment is considered to be effective.
paragraph 63. The method of paragraph 62, wherein the first sample and the second sample are urine samples.
paragraph 64. The method of paragraph 62 or 63, wherein the therapeutic agent is a P2Y14 inhibitor.
paragraph 65. The method of any one of paragraphs 62-64, wherein the subject is a human.
paragraph 66. A method of treating a subject determined to have a level of UDP-glucose above a reference level, the method comprising administering a treatment appropriate for treating renal inflammation.
paragraph 67. The method of paragraph 66, wherein the treatment appropriate for treating renal inflammation comprises a P2Y14 inhibitor.
paragraph 68. The method of paragraph 67, wherein the P2Y14 inhibitor is PPTN or an anti-P2Y14 antibody.
paragraph 69. The method of any one of paragraphs 66-68, wherein the subject is a human.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

As used herein, the term "renal inflammation" extends to all conditions which are substantially characterized by the occurrence of inflammation within the kidney, or where the occurrence of inflammation in the kidney is caused by a disease or an inflammatory condition which primarily affects a site in the body other than the kidney. In particular, inflammation may occur at a site including, but not limited to; the glomerulus, Bowman's capsule or Bowman's space. Typically, the inflammation results in at least partial impairment of kidney function and/or kidney failure.

Examples of specific conditions which fall within the meaning of the term "renal inflammation" include, but are not limited to: renal disorders which include, but are not limited to: chronic renal failure, acute renal failure, heterologous nephrotoxic nephritis, glomerulonephritis, sclerosis of the glomerulus, systemic lupus erythematosus (SLE), diabetic nephropathy, diabetic nephropathy wherein the diabetic nephropathy accompanies sclerosis of the liver, and glomerulonephritis wherein the glomerulonephritis is accompanied by sclerosis of the liver.

In some embodiments, renal inflammation can relate to an immune-mediated disease which affects the cells of the kidney and/or kidney function. Such conditions can include, but are not limited to: Immunoglobulin A nephropathy, membranoproliferative glomerulonephritis, mesangial proliferative glomerulonephritis, nonproliferative glomerulonephritis, membranous glomerulonephritis, minimal-change disease, primary focal segmental glomerulosclerosis (FSGS), fibrillary glomerulonephritis, immunotactoid glomerulonephritis, proliferative glomerulonephritis, progressive glomerulonephritis, anti-GBM disease, kidney ischemia, kidney vasculitis, including disease associated with anti-neutrophil cytoplasmic antibodies (ANCA) (e.g., Wegener granulomatosis), lupus nephritis cryoglobulinemia-associated glomerulonephritis, bacterial endocarditis, Henoch-Schönlein purpura, postinfectious glomerulonephritis, Hepatitis C, diabetic nephropathy, myloidosis, hypertensive nephrosclerosis, light-chain disease from multiple myeloma, secondary focal glomerulosclerosis, and hypertensive nephrosclerosis.

As used herein, the term "early stage" with respect to inflammation means that the tissue or organ exhibits minimal or mild damage resulting from inflammation. "Early stage inflammation" can mean a clinical stage of inflammation where substantial infiltration of pro-inflammatory cells and/or molecules into renal tissues has not occurred.

As used herein, the term "antibody" refers to an immunoglobulin molecule and immunologically active portions of immunoglobulin molecules, i.e., molecules that contain an antigen binding site that immunospecifically bind an antigen. The terms also refers to antibodies comprised of two immunoglobulin heavy chains and two immunoglobulin light chains as well as a variety of forms besides antibodies; including, for example, Fv, Fab, and F(ab')2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein can be manufactured using well-known methods, e. g., as described in Howard and Kaser "Making and Using Antibodies: A Practical Handbook" CRC Press (2006); which is incorporated by reference herein in its entirety.

The terms "antigen-binding fragment" or "antigen-binding domain", which are used interchangeably herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, "specific binding" can refer to an affinity of the first entity for the second target entity which is at least 10 times, at least 50 times, at least 100 times, at least 500 times, at least 1000 times or greater than the affinity for the third non-target entity. In some embodiments, "specific binding" refers to an antibody binding with a dissociation constant ($K_D$) of $10^{-5}$ M or less, $10^{-6}$ M or less, or $10^{-7}$ M or less, and binding to the predetermined antigen with a $K_D$ that is at least twofold less than its $K_D$ for binding to a nonspecific antigen other than the predetermined antigen.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the terms "inhibitor of P2Y14" or "P2Y14 inhibitor" refer to an agent that can decrease the expression level and/or activity of P2Y14, e.g. by at least 5%, at least 10%, at least 20%, at least 30%, at least 40%, at least 50%, at least 75%, at least 80%, at least 90%, at least 95%, at least 98%, at least 99% or more. It is preferred that an inhibitor of P2Y14 inhibits P2Y14 activity without substantially inhibiting other receptors or activities. It is also preferred that the specific inhibitory activity occurs at a concentration that is not toxic to the subject. In some embodiments, a P2Y14 inhibitor can decrease the level of P2Y14 mRNA, the level of P2Y14 polypeptide, and/or the level of signaling of P2Y14 in the cell of origin or a second cell. P2Y14 activity can be monitored, e.g., by measuring calcium influx and/or by measuring ligand binding. In some embodiments, a P2Y14 inhibitor can specifically bind a P2Y14 polypeptide. In some embodiments, a P2Y14 inhibitor can reduce signal transduction mediated by P2Y14. Irreversible or reversible inhibitors of P2Y14 can be used in the methods disclosed herein.

As used herein, the term "anti-P2Y14 antibody" means an antibody, e.g., an IgG molecule, that binds specifically to the extracellular portion of a full length P2Y14 polypeptide.

The terms "decrease", "reduce", "reduction", or "inhibit" are all used herein generally to mean a decrease by a statistically significant amount. However, for the avoidance of doubt, "decrease", "reduce", "reduction", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a decrease by a statistically significant amount in such level. The decrease can be, for example, at least 10%, at least 20%, at least 30%, at least 40% or more, and is preferably down to a level accepted as within the range of normal for an individual without a given disorder.

The terms "increased", "increase", or "enhance" are all used herein to generally mean an increase by a statically significant amount; for the avoidance of doubt, the terms "increased", "increase", or "enhance", can mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom is meant a statistically significant increase in such level.

As used herein, the terms "treat," "treatment," "treating," or "amelioration" refer to therapeutic treatments, wherein the object is to reverse, alleviate, ameliorate, inhibit, slow down or stop the progression or severity of renal inflammation. The term "treating" includes reducing or alleviating at least one adverse effect or symptom of renal inflammation. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. For example, treatment is considered effective if the extent or amount of renal inflammation is reduced, or the progression of renal inflammation is halted. In another example, treatment is considered effective if renal function is improved. The term "treatment" of a disease also includes providing relief from the symptoms or side-effects of the disease (including palliative treatment).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples.

The term "statistically significant" or "significantly" refers to statistical significance and generally means a two standard deviation (2SD) difference.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local. Therapeutic agents can be placed in a tissue or organ-specific delivery device. For example, a P2Y14 inhibitor can be placed in a renal catheter for direct delivery or to the renal circulation.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those disclosed herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

Example 1: Renal Intercalated Cells Sense and Mediate Sterile Inflammation Via the $P2Y_{14}$ Receptor Uncontrolled inflammation is one of the leading causes of kidney failure. Pro-inflammatory responses can occur in the absence of infection, a process called sterile inflammation. It is shown herein that the purinergic receptor P2Y14 (GPR105) is specifically and highly expressed in collecting duct intercalated cells (ICs), and mediates sterile inflammation in the kidney. P2Y14 is activated by UDP-glucose, a damage-associated molecular pattern molecule (DAMP) released by injured cells. Using transgenic mice expressing EGFP in ICs, as well as cultured cells, it was found that UDP-glucose activates the MEK1/2-ERK1/2 pathway, and increases pro-inflammatory chemokine expression. These effects were prevented following inhibition of P2Y14 with the small molecule PPTN. Tail vein injection of mice with UDP-glucose induced the recruitment of neutrophils to the renal medulla. This study identifies ICs as novel sensors, mediators and effectors of inflammation in the kidney via P2Y14.

In this study elevated expression of a restricted number of P2 receptors in ICs was uncovered, most notably P2Y14. Moreover, P2Y14 expression was not detectable in other renal epithelial cells. Evidence was also provided that P2Y14 activation by UDP-glucose induces a pro-inflammatory response in ICs that is mediated by activation of the MAPK pathway. This is followed by increased expression of pro-inflammatory chemokines in ICs, and subsequent neutrophil infiltration in the renal medulla. Thus, a novel inflammatory role for renal ICs via P2Y14 signaling has been identified.

Methods

Reagents and Antibodies

Uridine 5'-diphosphoglucose disodium salt hydrate from *Saccharomyces cerevisiae* (UDP-glucose) and the MEK inhibitor PD98059 were purchased from Sigma Aldrich (St. Louis, Mo.). Uridine diphospho-D-[6-$^3$H] glucose ([$^3$H] UDP-glucose) was purchased from Perkin Elmer (Waltham, Mass.). PPTN, a selective high affinity antagonist of the $P2Y_{14}$ receptor has been described previously (50). The chicken antibody against the V-ATPase B1 subunit has been described previously (72). An affinity-purified chicken antibody against the V-ATPase A subunit was raised against the same sequence as previously described for a rabbit anti-V-ATPase A subunit antibody and was found to have the same specificity (73, 74). A rabbit anti-P2Y14 antibody and its immunizing peptide were purchased from Alomone labs (Jerusalem, Israel). Rabbit anti-cytoskeletal actin antibody was from Bethyl Laboratory (Montgomery, Tex.). Rabbit anti-pendrin antibody was a kind gift from Dr. Aronson (Yale University). Rabbit monoclonal antibodies against p-p44/p42 MAPK and against total p44/p42 MAPK were purchased from Cell Signaling Technology (Boston, Mass.). Rat anti-Ly6G antibody was from Biolegend (San Diego, Calif.). Mouse anti-pan-actin was purchased from EMD Millipore (Billerica, Mass.). Affinity purified anti-rabbit HRP, anti-chicken HRP, anti-mouse HRP, anti-rabbit cy3 and anti-chicken cy3 were all raised in donkeys and purchased from Jackson Immunoresearch (West Grove, Pa.). Affinity purified anti-mouse HRP and anti-rabbit FITC were raised in goats and purchased from Jackson Immunoresearch. A goat anti-rat cy3 was from Invitrogen (Grand Island, N.Y.). Streptavidin-fluorescein was purchased from Invitrogen. Cell culture medium was purchased from Invitrogen, and bovine serum was purchased from Atlanta Biologicals (Lawrenceville, Calif.).

Animals

Adult male mice (eight to ten weeks old) were used for all experiments. Transgenic mice expressing EGFP under the promoter of the V-ATPase B1 subunit (B1-EGFP) mice have been described previously (35). Wild type (C57BL/6× CBAF1) mice were purchased from Jackson Laboratory (Bar Harbor, Me.). Animals were housed under standard conditions and maintained on a standard rodent diet. The Massachusetts General Hospital (MGH) Subcommittee on Research Animal Care approved all animal studies, in accordance with National Institutes of Health, Department of Agriculture, and Accreditation of Laboratory Animal Care requirements. For tail vein injections, animals were kept under isofluorane anesthesia (Baxter, Deerfield, Ill.) for several minutes to allow the injection of 200 µl of either saline solution or a saline solution containing 100 µM UDP-glucose (200 mg/kg of body weight).

Isolation of Intercalated Cells from Mouse Kidneys

Mice were anesthetized using pentobarbital sodium (50 mg/kg body, ip, Nembutal, Abbott Laboratories, Abbott Park, Ill.). The blood was flushed out of the organs by perfusing the animals with a phosphate-buffered saline (PBS) through the cardiac left ventricle at a constant flow rate of 17 ml/min. Kidneys were excised and sliced, and some kidneys were microdissected to separate the cortex from the medulla. Tissues were then minced immediately with scissors in RPMI 1640 medium (Invitrogen, Grand Island, N.Y.) containing 1.0 mg/ml collagenase type I (Invitrogen), 1.0 mg/ml collagenase type II (Sigma Aldrich) and 2 mg/ml hyaluronidase (Sigma Aldrich), and digested for 45 min at 37° C. A 40-µm-nylon mesh was used to remove undigested material following tissue digestion. Cells were then washed once with RPMI 1640 medium and once with a calcium-free PBS. EGFP-positive (EGFP(+)) and negative (EGFP(−)) cells were isolated immediately by FACS, based on their green fluorescence intensity, as described previously (36). Cell isolation was performed at the MGH flow cytometry core facility using a modified FACS Vantage cell sorter (BD Biosciences, San Jose, Calif.). FACS isolated samples were collected in PBS and used without delay for subsequent treatment and/or cell fractionation, protein and RNA isolation, or imaging.

RNA Isolation and RT-PCR

Total RNA was isolated from cells using RNeasy micro kit (Qiagen, Valencia, Calif.) and from tissues using RNeasy Mini kit, as described previously (36). DNase I digestion was performed using RNase-Free DNase Set (Qiagen) according to the manufacturer's instructions. All reverse transcription (RT) and PCR reagents were from Applied Biosystems (Foster City, Calif.). Reverse-transcription was performed for 1 h at 42° C. in a final volume of 50 µl with 1× buffer II, 5 mM $MgCl_2$, 1.0 mM each dNTP, 1 U/µl RNase inhibitor, 2.5 µM random hexamers, and 2.5 U/µl MuLV reverse transcriptase. PCR was performed on RT products. The sequences of the PCR primer sets, purchased from Invitrogen, are listed in Table 1. For end point PCRs, reaction mixtures consisted of a 20 µl final volume containing 2 μl template, 1.25 units AmpliTaq Gold DNA polymerase, 1× buffer II, 1.5 mM MgCl$_2$, 1.0 mM each dNTP, and 0.5 μM forward and reverse oligonucleotide primers. The following parameters were used for PCR: 8 min at 95° C. to activate the polymerase, 35 cycles of melting for 30 s at 95° C., annealing for 30 s at 60° C., extension for 30 s at 72° C., and a final extension for 10 min at 72° C. The amplification products were visualized by electrophoresis on a 1-2% agarose gel containing GelStar stain (Lonza, Rockland, Me.).

Real Time PCR was performed with a 7300 Real Time PCR system (Applied Biosystems). Amplification products were detected using the Power SYBR Green PCR master mix (Applied Biosystems), according to the manufacturer's instructions. Standard-curve relative quantifications were performed and relative values of each sample were normalized to GAPDH values. Samples were analyzed in triplicates for each experiment.

Flow Cytometry Analysis

Tissues and cells were prepared as described above for FACS. Prior to flow cytometry, cell suspensions were stained in PBS with BSA 1% using the following antibodies purchased from BD Biosciences (San Jose, Calif.): PE-conjugated anti-CD90 (clone 53-2.1), PE-conjugated anti-B220 (clone RA3-6B2), PE-conjugated anti-CD49b (clone DX5), PE-conjugated anti-NK1.1 (clone PK136), PE-conjugated anti-Ly-6G (clone 1A8), APC-Cy7-conjugated anti-CD11b (clone Ml/70), PE-Cy7-conjugated anti-F4/80 (clone BM8), Alexa Fluor 700-conjugated anti-CD11c (clone HL3). Antibodies purchased from BD Pharmigen were also used: PE-conjugated anti-CD19 (clone 1D3), PE-Cy7-conjugated anti-B220 (clone RA3-6B2), FITC-conjugated anti-CD3e (clone 145-2C11), PE-Cy7-conjugated anti-CD4 (clone RM4-5) and PerCP-conjugated anti-CD8a (clone 53-6.7). Single cell suspensions were labeled for 45 min at 4° C. For monocyte/neutrophil staining, the following PE-conjugated antibodies were used: anti-CD90, anti-B220, anti-CD19, anti-CD49b, anti-NK1.1 and anti-Ly-6G. Neutrophils were defined as Lin+CD11b+ cells. B cells were defined as B220+CD19+ cells. Total T cells were defined as CD3e+ cells. CD4 T cells were defined as CD3e+CD4+ cells. CD8 T cells were defined as CD3e+CD8a+ cells. The number of neutrophils, B and T cells was defined as the total number of cells per organ multiplied by the percentage of each cell type identified by flow cytometry (LSRII; BD Biosciences). Cell suspensions obtained from the spleen were labeled with appropriate antibodies for staining controls. Data were analyzed with FlowJo v.8.8.7 (Tree Star, Inc., Ashland, Oreg.).

Cell Culture and Protein Preparation

MDCK-C11 cells were cultured at 37° C. in a 5% CO2-95% O2 mix in DMEM (Invitrogen) supplemented with 2 mM glutamine, 10% fetal bovine serum (Invitrogen), penicillin (100 U/ml), and streptomycin (100 μg/ml) (Invitrogen). Prior to any treatment, cells were serum starved for 24 hours. For cell surface biotinylation assays, cells were either grown to confluence on plastic dishes or on filters. Biotinylation was performed as described previously (75). Briefly cells were incubated with 1 mg/ml of biotin (Thermo Scientific, Pittsburgh, Pa.) in PBS pH 8 on ice for 1 h. The excess biotin was quenched with 100 mM glycine and cells were either further processed for immunostaining or lysed in lysis buffer [150 mM NaCl, 5 mM EDTA, 50 mM Tris/HEPES, pH 7.5; 1% (vol/vol) Triton X-100] containing protease and phosphatase inhibitors (Complete Mini EDTA free, PhosSTOP, Roche Diagnostics, Laval, Canada), for 20 min at 4° C. Total protein expression was determined in 2-5 μg of proteins from the total cell extracts. 50-100 μg of cell lysate proteins were incubated with neutravidin beads (Thermo Scientific) overnight at 4° C. (according to the manufacturer's protocol). After centrifugation (2,500 g for 5 min) and removal of the supernatant, beads were washed three times with the lysis buffer, twice with a high-salt buffer (500 mM NaCl, 5 mM EDTA, 50 mM Tris, 0.1% Triton X-100, pH 7.5) and once with a no-salt buffer (10 mM Tris, pH 7.5). Proteins were subjected to SDS-PAGE following denaturation in Laemmli buffer for 5 min at 95° C. For enzymatic deglycosylation, 20 μg of total and 100 μg of biotinylated and avidin precipitated proteins were treated for 1 h at 37° C. with either endoglycosydase H or PNGase F or control according to the manufacturer's protocol (New England Biolabs, Ipsxich, Mass.). For P2Y$_{14}$ antagonist studies, PPTN was dissolved in DMSO and applied to confluent MDCK-C11 cells at a final concentration of 10 μM (0.05% DMSO). Pretreatment with PPTN or vehicle (0.05% DMSO) was for 30 minutes prior to control or UDP-glucose treatment.

Radioligand Binding Assays

[$^3$H]UDP-glucose binding assays were performed in MDCK-C11 cell line and FACS isolated IC membrane preparations, as previously described (16). Confluent MDCK-C11 cells were scrapped in ice-cold PBS, pelleted by centrifugation (500 g, 10 min) and then resuspended in 1 ml ice-cold Tris-acetate 0.2 M buffer (pH 7.5) containing protease inhibitors (Complete Mini, Roche, Indianapolis, Ind.) using a 25G needle. Cell membranes were harvested by passing through a cell cracker (HGM lab equipment, Heidelberg, Germany) 10 times. The solution was then centrifuged 10 min at 17000 g and membrane pellets were frozen in liquid nitrogen and kept at −80° C. until use. Protein concentration was determined using a nanodrop 2000 (Thermo scientific).

For dose-displacement assays 15 μg of MDCK-C11 cell membrane proteins were incubated for 3 hours at 22° C. in a medium containing 50 mM Tris/HCl pH 7.4, 1 mM EDTA, 5 mM MgCl2 and BSA (5 mg/ml), [$^3$H]-UDP-glucose (3 nM) and selected concentrations of UDP-glucose or ATP. Incubation was terminated by the addition of ice-cold 50 mM Tris/HCl pH 7.4, 1 mM EDTA, 5 mM MgCl$_2$ and was followed immediately by filtration under vacuum through Gelman A/E glass filters (Pall life science, An Arbor, Mich.) pre-soaked in binding buffer. The filters were rinsed twice before the addition of 5 ml of scintillation fluid (OpticFluor, Groninge, The Netherlands). Receptor-bound radioactivity was measured using liquid scintillation analyzer Tricarb 2200 CA from Parckard. All assays were performed in triplicate. [$^3$H]UDP-glucose binding assays were also performed in isolated EGFP(+) and EGFP(−) cells. Membranes were incubated with a saturating concentration of [$^3$H]UDP-glucose for 3 hours at 22° C. The non-specific [$^3$H]UDP-glucose binding was determined in the presence of 10 μM unlabeled UDP-glucose. The specificity of [$^3$H]UDP-glucose binding was demonstrated in the presence of a saturating concentration of ATP (10 μM). Incubations were stopped by the addition of ice-cold buffer and receptor-bound radioactivity was determined as described above. The equilibrium dissociation constant (Kd) and the capacity of binding in dose-displacement studies were calculated using a scatchard plot and are expressed as the mean±SD. Statistical analysis were performed using the unpaired Student t-test.

Immunoblotting

Proteins were run on NuPAGE Novex bis/tris 4-12% gels (Invitrogen) and transferred to nitrocellulose membranes (Bio-Rad). After blocking (5% BSA in TBS 0.1% Tween 20 for 1 h), membranes were incubated overnight with the primary antibody, as indicated in the text. After 3 washes in TBS 0.1% Tween 20, horseradish peroxidase-conjugated secondary antibodies diluted 1:10,000 in TBS 0.1% Tween 20 were applied for 1 h at RT. Membranes were assayed with Western Lightning Chemiluminescence reagent (Perkin Elmer Life Sciences, Waltham, Mass., USA) and Kodak imaging films.

Immunofluorescence

Mice were anesthetized using pentobarbital sodium (50 mg/kg body, ip). The left kidney was perfused through the renal artery with PBS (0.9% NaCl in 10 mM phosphate buffer, pH 7.4), followed by paraformaldehyde-lysine-periodate fixative (PLP; 4% paraformaldehyde, 75 mM lysine-HCl, 10 mM sodium periodate, and 0.15 M sucrose, in 37.5 mM sodium phosphate) for 10 min at a constant rate of 3.5 ml/min. Kidneys were further fixed by immersion in PLP for 4 h at room temperature and subsequently overnight at 4° C. After extensive washes in PBS, cryo-protection was performed in PBS containing 0.9 M (30% wt/vol) sucrose overnight at 4° C. Prior to cryo-sectioning, tissues were embedded in Tissue-Tek OCT compound 4583 (Sakura Finetek USA, Torrance, Calif.) and frozen at −20° C. Sections (4-10 μm) were cut on a Leica CM3050-S cryostat (Leica Microsystems, Bannockburn, Ill.) and stored at 4° C. until use (37, 72). Sections were rehydrated in PBS and antigen retrieval techniques were performed by microwave heating in alkaline solution (10 mM Tris buffer, 1 mM EDTA, pH 9.0) 3 times for 1 min, with 5 min interval and then cooled down to room temperature. Sections were then treated with 1% (wt/vol) SDS for 4 min (76). After washes in PBS, and incubation for 20 min in 1% (wt/vol) BSA in PBS the sections were incubated for 60 min or overnight at 4° C. with the primary antibody diluted in PBS containing 1% BSA. The secondary antibody was applied for 1 h at room temperature and slides were mounted in Vectashield H1200 medium containing 4,6-diamidino-2-phenylindole (DAPI) (Vector Laboratories, Burlingame, Calif.). Digital images were acquired using a Nikon 90i epifluorescence microscope (Nikon Instruments, Melville, N.Y.). Images were analyzed using Volocity version 6.2.1 image-processing software (Perkin Elmer), and imported into Adobe Photoshop software as TIFF files and the levels command was applied to the entire field of view to better represent the raw data visualized under the microscope.

MDCK-C11 cells grown to confluence on filter (Corning) were biotinylated as described above and were then fixed for 30 min in 4% paraformaldehyde (Electron Microscopy Sciences, Hatfield, Pa.). Cells were washed three times with PBS and treated with 1% SDS for 4 min for antigen retrieval. After several washes in PBS and blocking of the proteins with 1% BSA for 30 min, cells were incubated for 1 h with anti-P2Y$_{14}$ antibody diluted 1:200 in PBS containing 1% BSA. Donkey anti-rabbit Cy3-conjugated antibody (1:800) and FITC-conjugated streptavidin (1:1000) were applied for 40 min at RT. After three washes with PBS, cells were mounted with Vectashield (Vector Laboratories) and visualized with a Zeiss Radiance 2000 laser scanning confocal microscope (Zeiss Laboratories) using LaserSharp 2000 version 4.1 software. Z-series (0.25 μm interval) were taken for X-Z side view representations.

Statistical Analysis

The effects of treatments between two groups were determined by unpaired Student's t-test when appropriated. Comparisons between multigroups were determined by one-way ANOVA followed by a post-hoc t-test. All tests were two-tailed, and P<0.05 was considered as statistically significant.

Results

P2 Receptor mRNA Expression in Intercalated Cells

P2X and P2Y receptor mRNA expression was first analyzed by conventional RT-PCR in IC-enriched EGFP(+) cells isolated by FACS from the kidneys of B1-EGFP mice as well as in whole kidney. In these mice, EGFP expression is driven by the promoter of the V-ATPase B1 subunit, and occurs specifically in type A intercalated cells (A-ICs), type B intercalated cells (B-ICs), and in the connecting tubules (CNT) (35). It was previously shown that a highly enriched EGFP(+) cell preparation could be generated that is depleted from all other cell types after FACS isolation (36, 37). As shown in FIG. 1, while transcripts specific for all P2 receptors, except P2Y4, were detected in whole kidney extracts (bottom panel), this number was narrowed down to 3 P2X (P2X$_1$, P2X$_4$ and P2X$_5$) and 3 P2Y (P2Y$_2$, p2y5 and P2Y$_{14}$) receptors in EGFP(+) cells (FIG. 1, top panel).

Figure 2A:
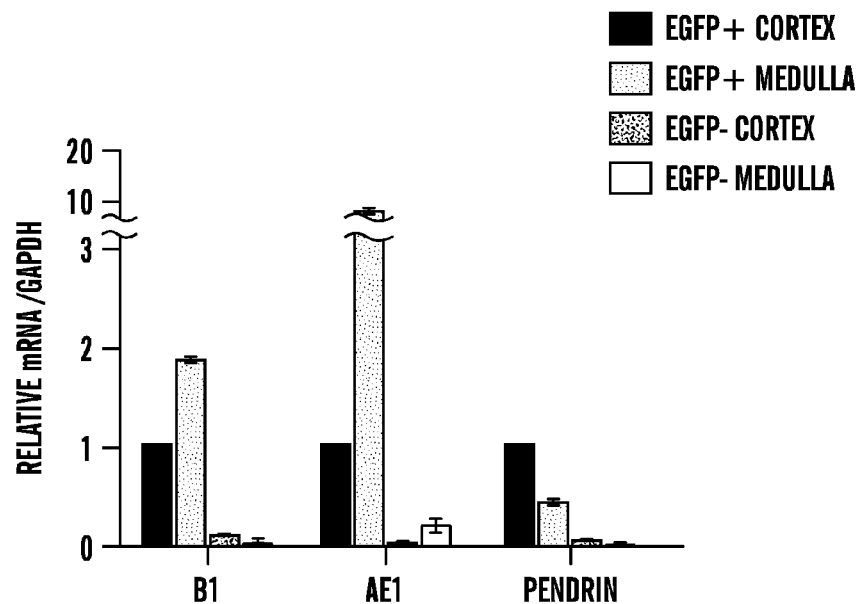
FIG. 2A is a bar graph showing quantitative PCR detection of IC markers (B1, AE1, pendrin,) in EGFP(+) vs EGFP(−) cells isolated from renal cortex and medulla. Values are normalized to GAPDH and represented as fold changes relative to the values obtained in cortical EGFP(+) cells.
Figure 2B:
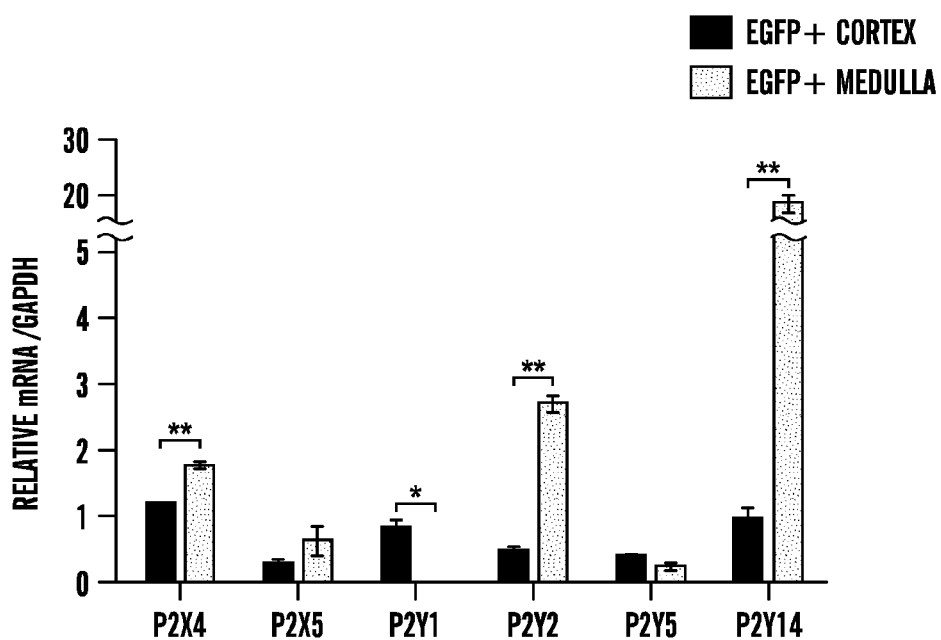
FIG. 2B is a bar graph showing relative P2 receptor mRNA levels, analyzed by quantitative PCR in medullary and cortical EGFP(+) cells. Data are normalized for GAPDH and are expressed as mean±SEM (n=3), *P<0.05, **P<0.001.

The regional separation of B-ICs and CNT cells relative to A-ICs was exploited. B-ICs and CNT cells are located exclusively in the renal cortex and to a lesser extent in the outer stripe of the outer medulla (OS), and A-ICs are located in most kidney regions (except the tip of the papilla) (38, 39). A mixed EGFP(+) cell population containing A-ICs, B-ICs and CNT cells was isolated from the kidney cortex and was compared with a "pure" A-IC population isolated from the inner stripe of the outer medulla (IS) and inner medulla. Quantitative PCR showed a marked enrichment of mRNA transcripts specific for the V-ATPase B1 subunit (a marker of A-ICs, B-ICs and CNT cells) (40-42), AE1 (a marker of A-ICs) (43) and pendrin (a marker of B-ICs) (44, 45) in EGFP(+) cells compared to EGFP(−) cells isolated from the same regions (FIG. 2A). As expected, an increase in AE1 mRNA and a decrease in pendrin mRNA were detected in EGFP(+) cells isolated from the medulla versus the cortex, respectively, demonstrating the enrichment of A-ICs in the medullary EGFP(+) cells versus cortical EGFP(+) cell populations. Quantitative PCR showed significantly higher expression levels for P2X$_4$, P2Y$_2$ and P2Y$_{14}$ in EGFP(+) cells isolated from the medulla compared to the cortex (FIG. 2B). P2X$_5$ and p2y5 expression appeared to be similar in both regions and P2Y$_1$ was detectable only in cortical EGFP(+) cells, suggesting that A-ICs most probably do not express P2Y$_1$. The very high P2Y$_{14}$ enrichment (by more than 20 fold) that was measured in medullary EGFP(+) cells compared to cortical EGFP(+) cells prompted further characterization of the role of this receptor in ICs.

P2Y14 is Exclusively Expressed in Intercalated Cells

Figure 3A:
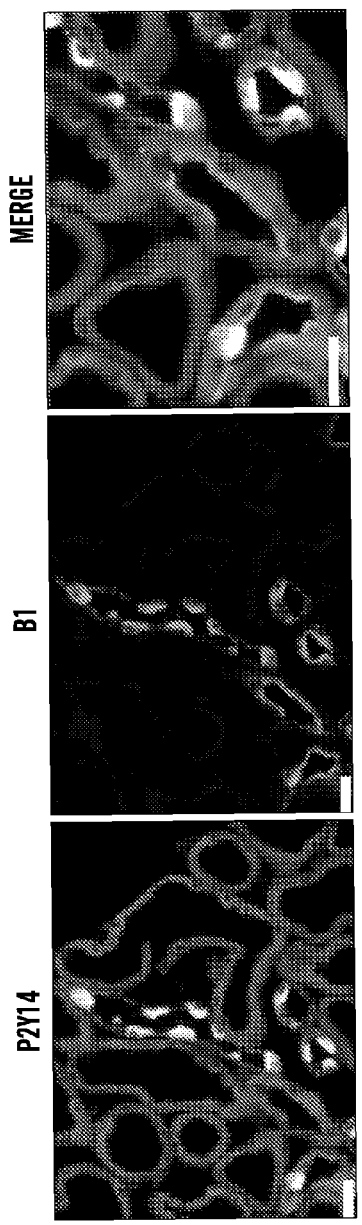
FIGS. 3A-3D are images showing immunofluorescence localization of $P2Y_{14}$ in mouse kidney. Cortical (FIG. 3A) and medullary (FIG. 3B) sections double-labeled for $P2Y_{14}$ (visualized as green) and the V-ATPase B1 subunit (visualized as red). $P2Y_{14}$ was detected in intercalated cells (ICs) identified by their positive labeling for the V-ATPase (visualized as yellow in the merge panel shown in FIG. 3A). No $P2Y_{14}$ was detected in distal tubule cells, which also express the V-ATPase (visualized as red in the merge panel shown in FIG. 3A). The $P2Y_{14}$ staining was abolished after preincubation of the $P2Y_{14}$ antibody with its immunizing peptide in the cortex (FIG. 3C) and medulla (FIG. 3D). Scale bars=25 μm.
Figure 3B:
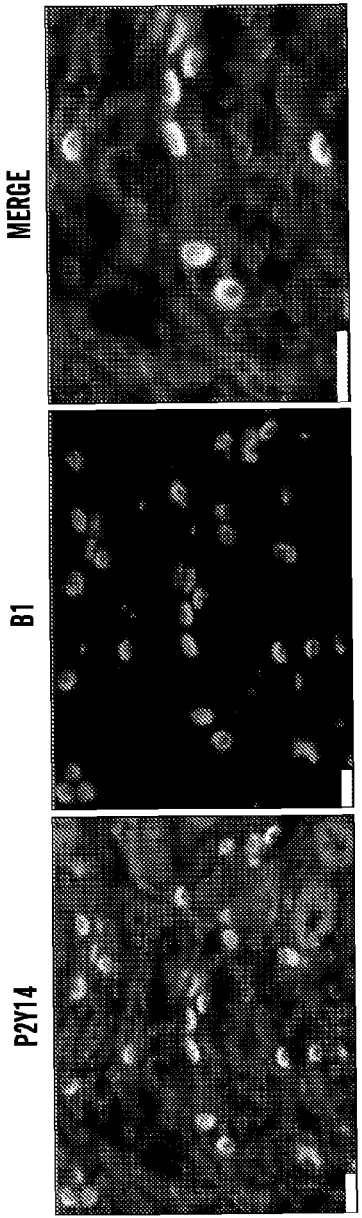
Figure 3C:
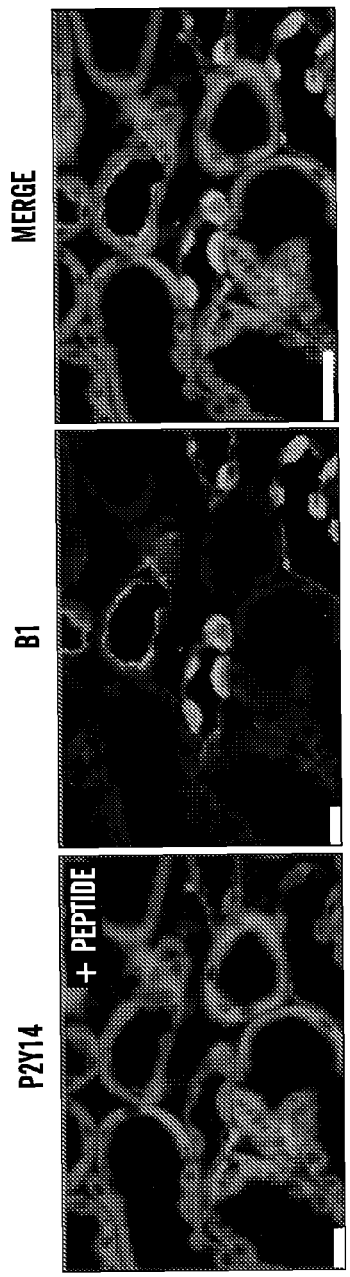
Figure 3D:
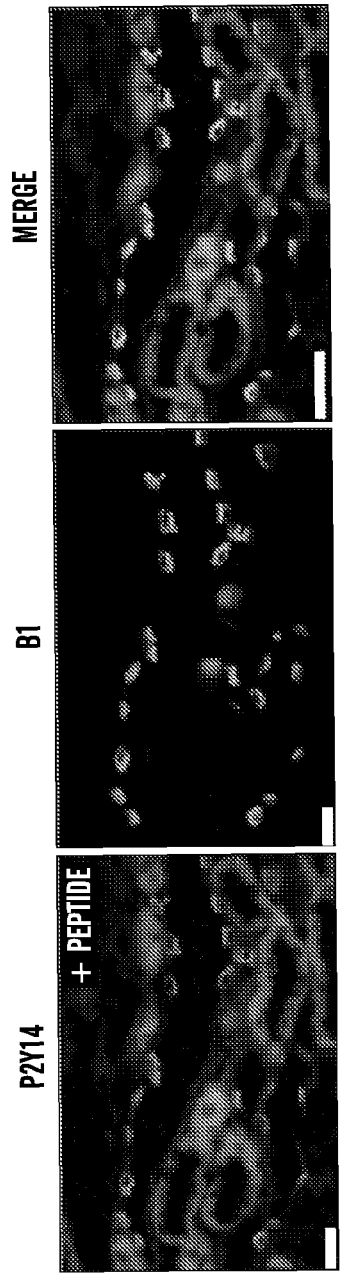
Figure 4B:
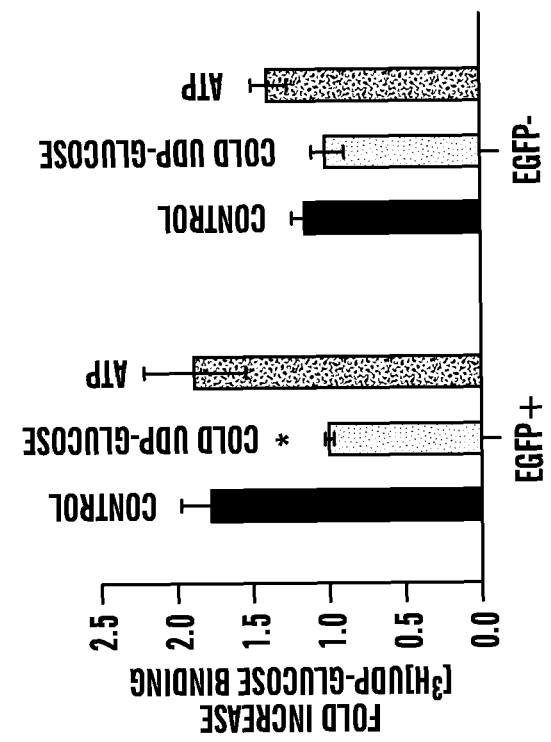
FIGS. 4A-4B are experimental data showing the expression of $P2Y_{14}$ in EGFP(+) cells.
Figure 4A:
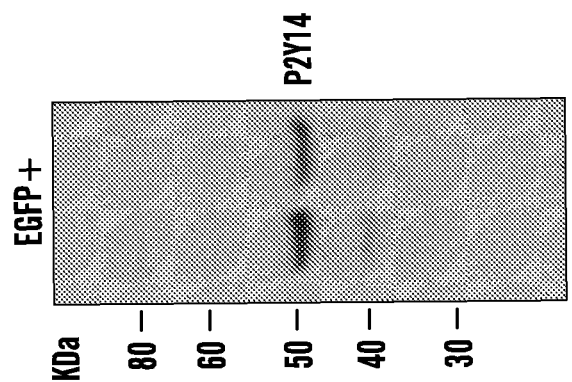

Double-immunofluorescence labeling of kidney sections for P2Y$_{14}$ (visualized as green) and the V-ATPase B1 subunit (visualized as red) showed specific expression of P2Y$_{14}$ in A-ICs and B-ICs in the cortex, while no P2Y$_{14}$ was detected in the distal and connecting tubules (FIG. 3A). In the medulla, P2Y$_{14}$ was detected only in A-ICs (FIG. 3B). P2Y$_{14}$ was expressed in the apical region of both A-ICs and B-ICs, as compared to the V-ATPase B1 subunit, which is apical in A-ICs, but basolateral or bi-polar in B-ICs (40). Pre-incubating the P2Y$_{14}$ antibody with its immunizing peptide abolished the P2Y$_{14}$ staining in both the cortex (FIG. 3C) and medulla (FIG. 3D). P2Y$_{14}$ was also detected in occasional immune cells, which remained attached to the blood vessel walls (data not shown), consistent with its previously described localization in circulating immune cells (28-30). Immunoblotting of EGFP(+) cell extracts with the P2Y14 antibody showed a predominant 50-KDa band and a weaker 40-kDa band (FIG. 4A). A radiolabeled UDP-glucose binding assay was then performed using total membranes separated from FACS isolated EGFP(+) cells and EGFP(−) cells (FIG. 4B). The [$^3$H]UDP-glucose binding measured in EGFP(+) cells was displaced with a saturating concentration of cold UDP-glucose [$10^{-5}$ M], but not with ATP [$10^{-5}$ M], showing UDP-glucose-specific binding. In contrast, in EGFP(−) cells no UDP-glucose-specific binding was measured. Altogether, these data show that ICs are the only renal epithelial cells that express $P2Y_{14}$.

UDP-Glucose Enhances ERK1/2 Phosphorylation in ICs

Figure 5A:
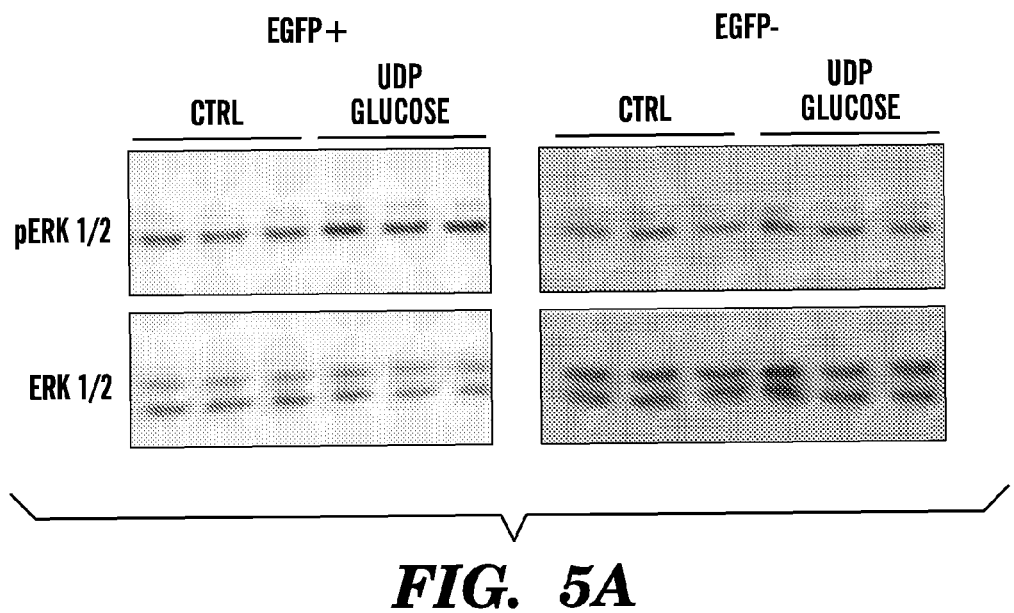
FIGS. 5A-5B are experimental data showing the effect of UDP-glucose on ERK1/2 phosphorylation in FACS isolated EGFP(+) and EGFP(−) cells.
Figure 5B:
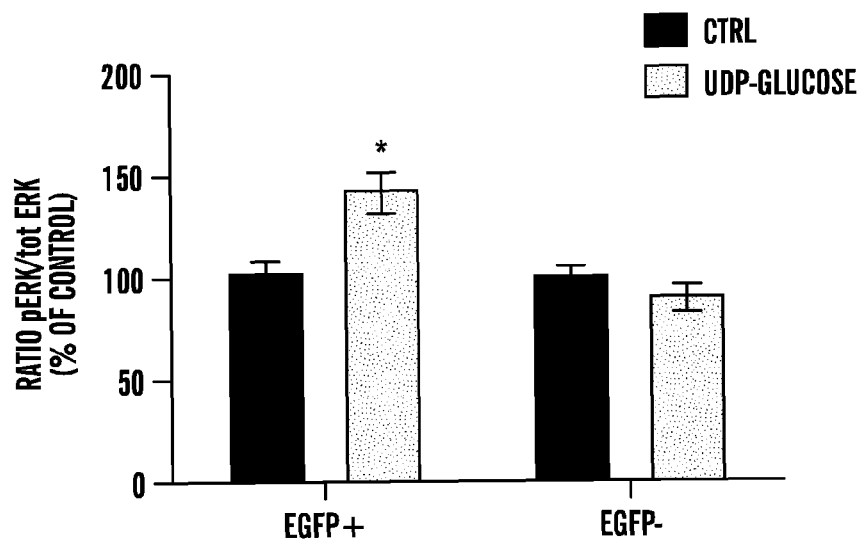

In human embryonic kidney (HEK) 293 cells stably transfected with $P2Y_{14}$, UDP-glucose stimulates the mitogen activated protein kinase (MAPK) pathway to phosphorylate extracellular signal-regulated kinase (ERK)1/2 (46). It was, thus, tested whether this pathway was activated by UDP-glucose in ICs. FACS-isolated EGFP(+) ICs were treated in vitro with 100 μM UDP-glucose for 15 min and ERK1/2 phosphorylation was measured by WB. FIGS. 5A-5B show a significant increase in ERK1/2 phosphorylation following UDP-glucose treatment in EGFP(+) cells (left panel). No increase in ERK-phosphorylation was seen in EGFP(−) cells (FIG. 5A, right panel), confirming the specificity of $P2Y_{14}$ activation by UDP-glucose in ICs. Quantification showed a significant increase in ERK1/2 phosphorylation in EGFP(+) cells but not in EGFP(−) cells (FIG. 5B).

Characterization of the $P2Y_{14}$ Signaling Pathway in the Renal Epithelial Cell Line MDCK-C11

Figure 6A:
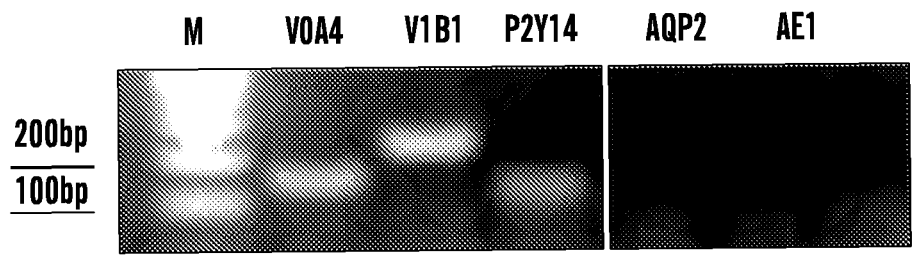
FIGS. 6A-6F are experimental data showing P2Y14 expression in MDCK-C11 cells.
Figure 6B:
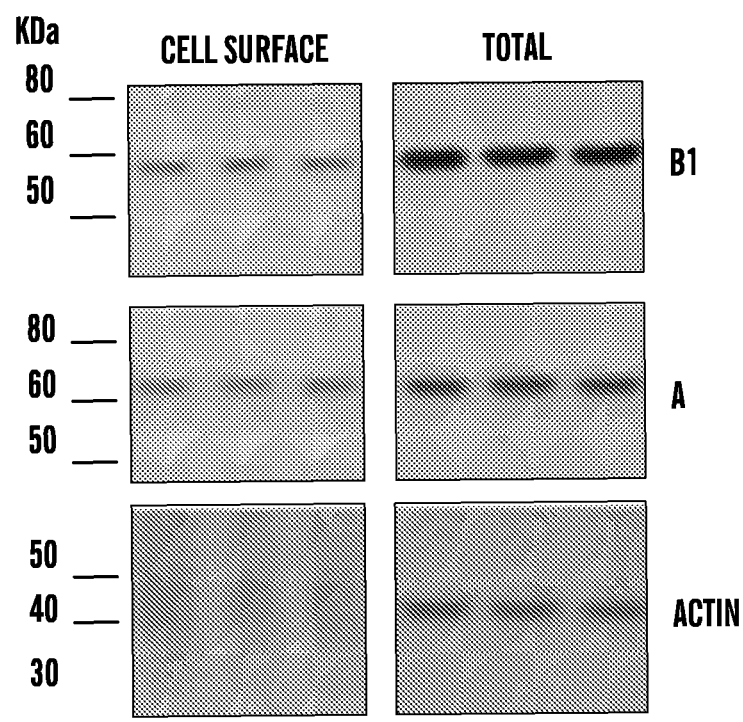
Figure 6C:
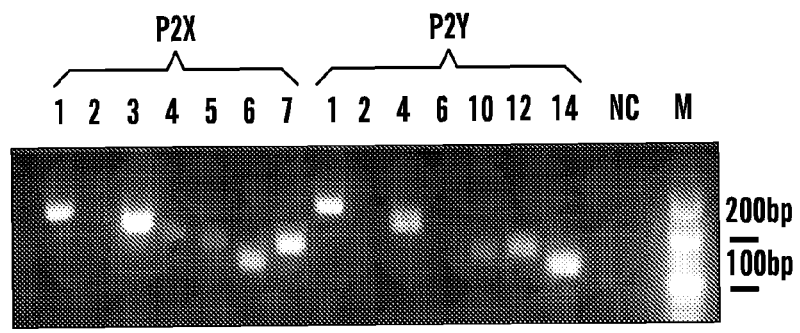
Figure 6D:
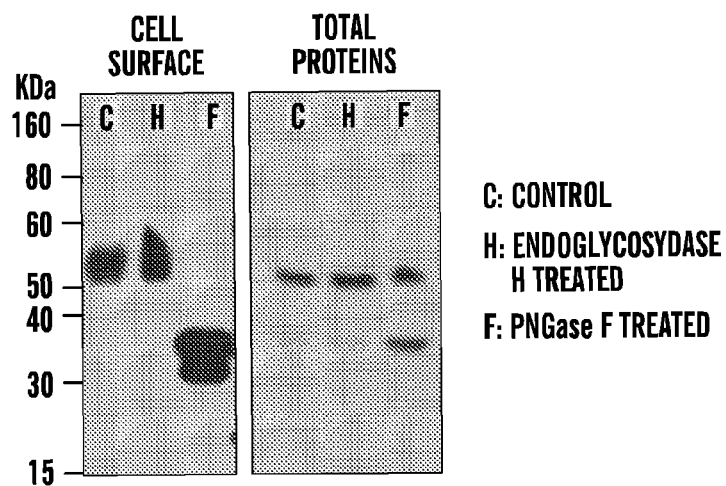
Figure 6E:
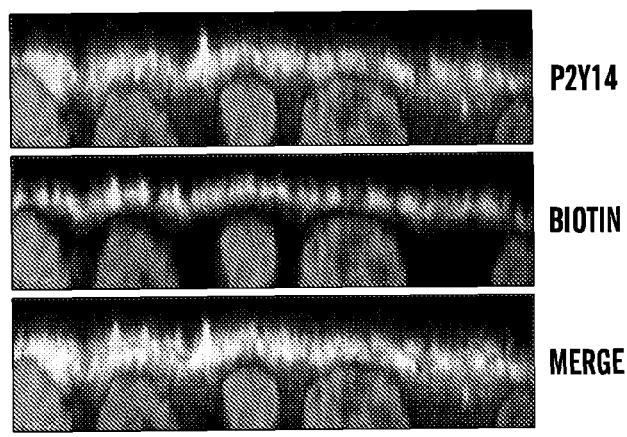
Figure 6F:
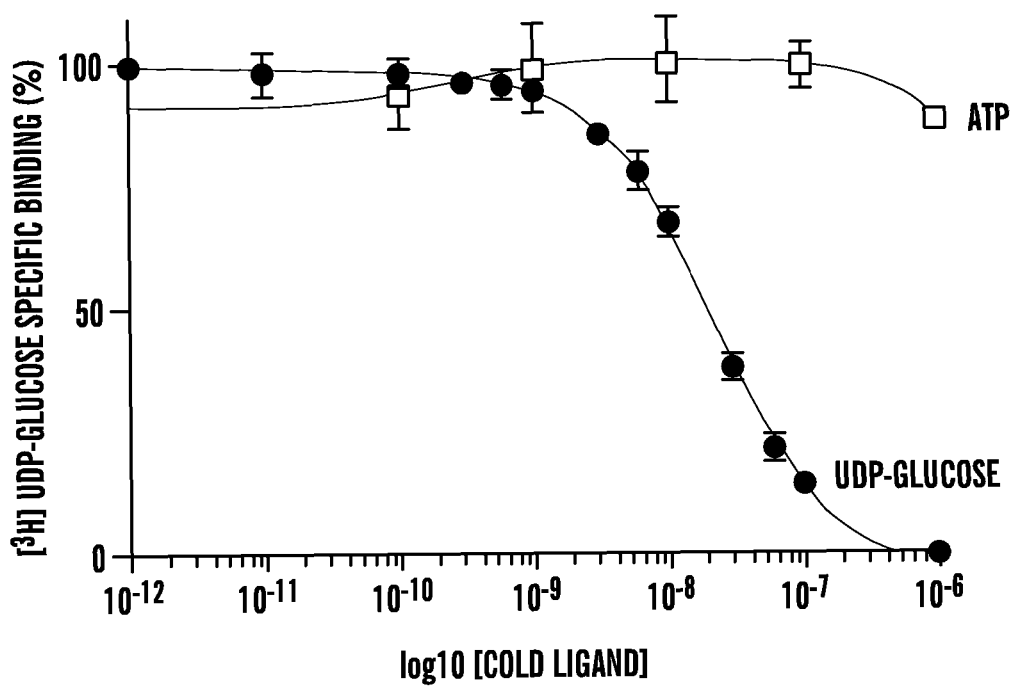

The Madin-Darby Canine Kidney (MDCK) subclone C11 (MDCK-C11) was first used as a renal epithelial cell model for the initial identification and characterization of the $P2Y_{14}$ signaling pathway. MDCK-C11 cells were previously shown to possess some characteristics of ICs, including Cl$^-$ and H$^+$ secretion and the activation of H$^+$ secretion by cAMP (47). In agreement with this notion, RT-PCR analysis showed expression of markers of ICs, including the V-ATPase B1 and a4 subunits in these cells (FIG. 6A). AQP2, a marker of collecting duct principal cells, was not detected, supporting their non-principal cell phenotype (47). MDCK-C11 cells did not express AE1 and thus do not retain all characteristics of A-ICs. However, expression in MDCK-C11 cells of the V-ATPase B1 and A subunits was confirmed at the protein level by western blotting, in total cell lysates and in a biotinylated plasma membrane protein fraction (FIG. 6B). The membranes were re-blotted for actin. The absence of actin staining in the cell surface preparation showed the absence of biotin contamination of intracellular proteins in this sample. RT-PCR analysis showed transcripts specific for $P2Y_1$, $P2Y_4$, p2y10, $P2Y_{12}$ and $P2Y_{14}$ (FIG. 6C). With the exception of $P2X_2$ all other P2X receptors were also detected. Western blotting analysis showed expression of $P2Y_{14}$ protein in total cell lysates and at the cell surface (FIG. 6D). In agreement with a previous report in glioma C6 cells (48), a more diffuse band at higher molecular weight was detected in the plasma membrane compared to the 50 kDa band in total cell lysates, indicating that only the glycosylated receptor can reach the cell surface. Glycosylation of $P2Y_{14}$ was confirmed by PNGaseF treatment, which resulted in the appearance of the deglycosylated form of $P2Y_{14}$ at around 45 KDa in total cell lysates and in cell surface protein extracts. Confocal microscopy showed $P2Y_{14}$ localization in the apical plasma membrane (visualized as red), which was biotinylated and labeled with biotin (visualized as green) in MDCK-C11 cells grown on filters (FIG. 6E). $P2Y_{14}$ is also expressed in the sub-apical region of the cells. The functionality of the receptor in MDCK-C11 cells was then investigated by using a radiolabeled UDP-glucose binding assay. The specificity of UDP-glucose binding was analyzed by dose-displacement of [$^3$H]UDP-glucose in the presence of unlabeled UDP-glucose or ATP. As shown in FIG. 6F, the addition of increasing concentrations of unlabeled UDP-glucose diminished [$^3$H]UDP-glucose binding in a dose-dependent manner. Concentration of ATP of up to 10 μM had no significant inhibitory effect on the [$^3$H]UDP-glucose binding. Scatchard analysis of the binding shows only one class of binding site with an affinity of 11.5±1.3 nM and a maximal binding capacity of 16.0±0.2 pmol/mg of protein. These values are very similar to the values obtained in HEK-293 cells expressing $P2Y_{14}$ (previously known as KIAA0001) (16).

UDP-Glucose Increases ERK1/2 Phosphorylation Through $P2Y_{14}$ Activation in MDCK-C11 Cells.

Figure 7A:
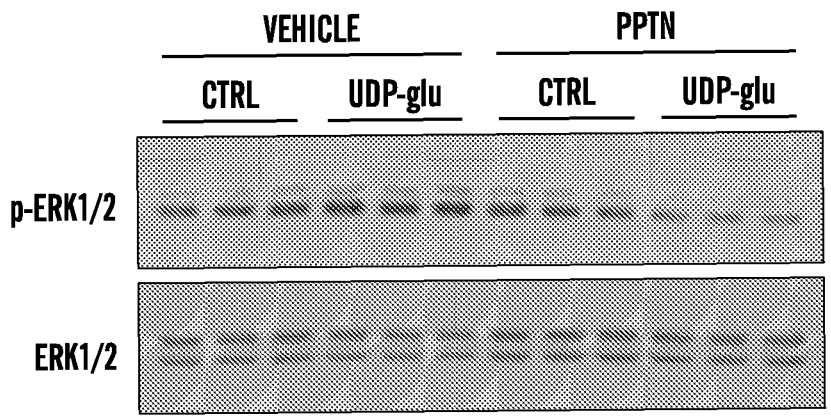
FIGS. 7A-7B are experimental data showing P2Y$_{14}$ activation by UDP-glucose increases ERK1/2-phosphorylation in MDCK-C11 cells.
Figure 7B:
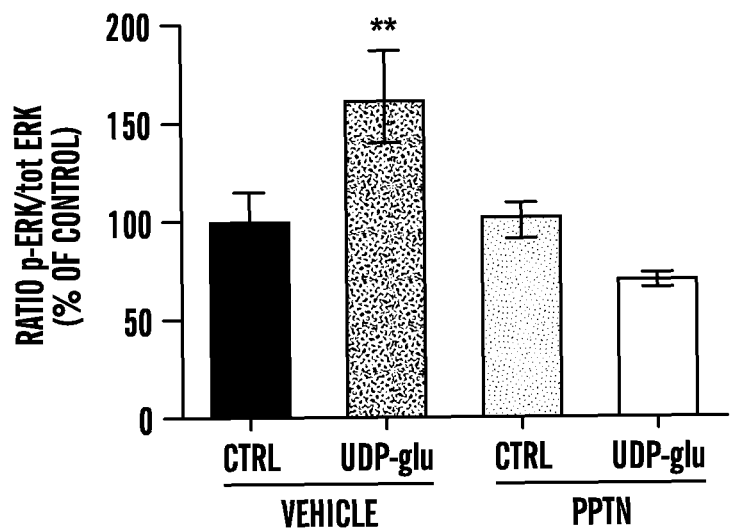

As shown in FIG. 7A (upper panel), UDP-glucose (100 μM) induced a significant increase in ERK1/2 phosphorylation in MDCK-C11 cells. This was prevented by pretreatment with the P2Y14 antagonist, 4-((piperidin-4-yl)-phenyl)-(7-(4-(trifluoromethyl)-phenyl)-2-naphthoic acid (PPTN, 10 μM). Quantification of the ratio of p-ERK1/2 to total ERK1/2 showed a significant increase in ERK1/2 phosphorylation following UDP-glucose treatment, which was abolished in the presence of PPTN (FIG. 7B, bottom panel). An increase in the phosphorylation of other MAPK targets such as p38 and JNK/SAPK (data not shown) was not detected, consistent with a previous report (46).

Figure 8A:
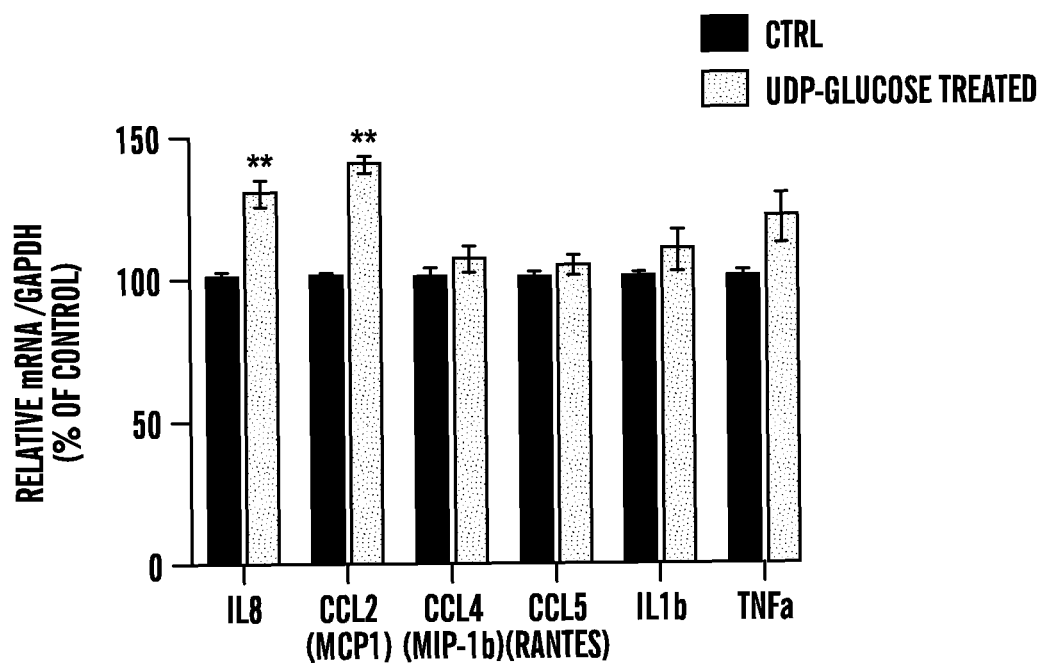
FIG. 8A shows quantitative PCR detection of pro-inflammatory mediators in MDCK-C11 cells under control conditions and 4 h after 100 μM UDP-glucose treatment. Data are represented as % changes relative to control. All values are normalized to GAPDH and are shown as Means±SEM (n=5), ** P<0.001.
Figure 8B:
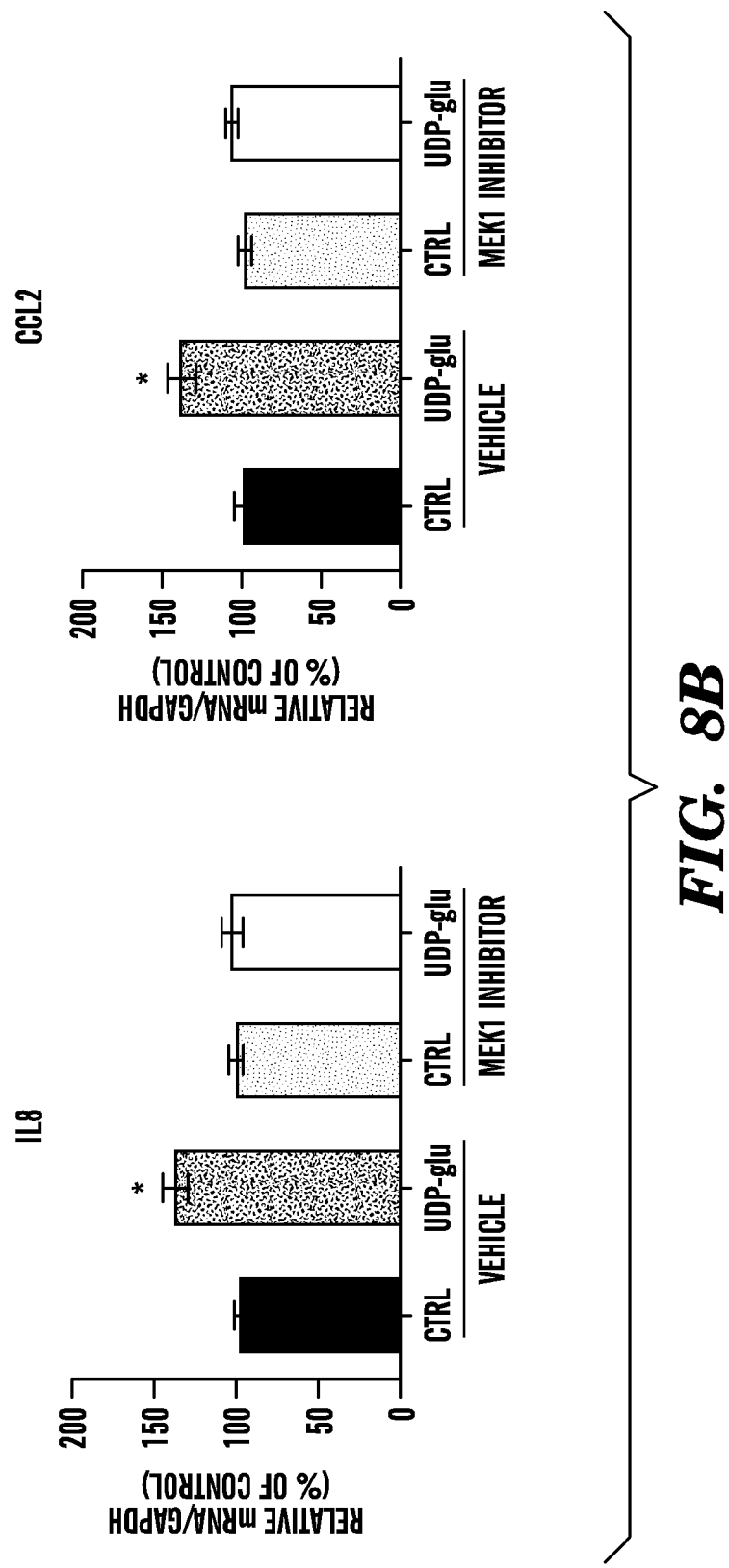
FIG. 8B shows quantification of changes in IL-8 (left) and CCL2 (right) mRNA expression in MDCK-C11 cells pretreated with the vehicle only or with the MEK inhibitor, PD98059 (50 μM) for 30 minutes in the absence (CTRL) or presence of 100 tM UDP-glucose (UDP-glu).
Figure 8C:
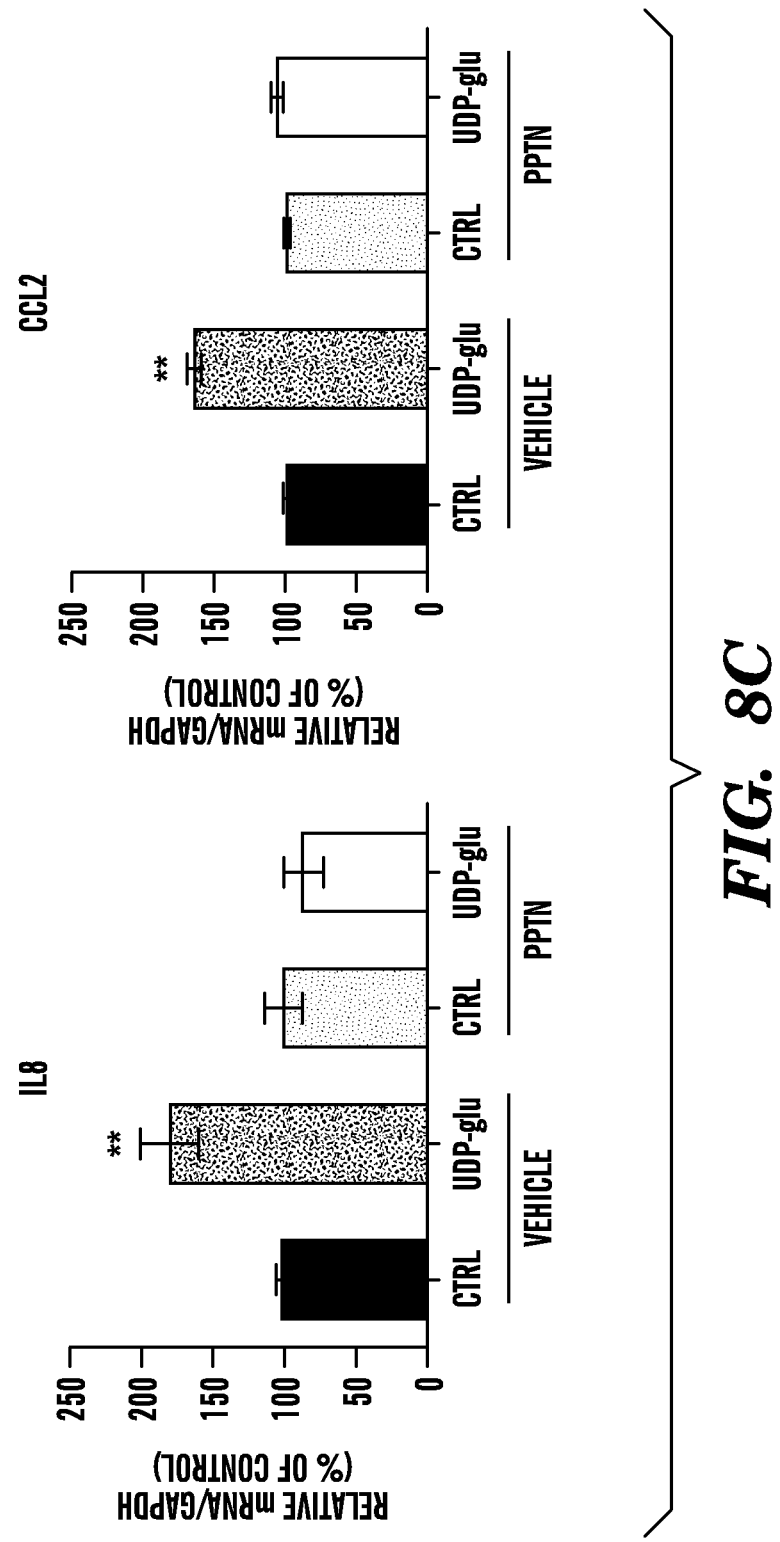
FIG. 8C shows quantification of changes in IL-8 (left) and CCL2 (right) mRNA expression in MDCK-C11 cells pretreated with the vehicle only or with PPTN (10 tM) for 30 minutes, in the absence (CTRL) or presence of 100 tM UDP-glucose (UDP-glu). Data are represented as % changes relative to control. Values are means±SEM (n=3), * P<0.05, **P<0.001.

P2Y14 Activation Up-Regulates Pro-Inflammatory Chemokine mRNAs Through ERK-Phosphorylation The effects of $P2Y_{14}$ activation with UDP-glucose on mRNA expression of several pro-inflammatory chemokines and cytokines were assessed here, both in MDCK-C11 cells (FIGS. 8A-8C) and renal EGFP(+) cells isolated by FACS from B1-EGFP mice (see below). As shown in FIG. 8A, MDCK-C11 cells increased IL-8 and CCL-2 mRNA expression following 4 h treatment with 100 μM UDP-glucose. IL-8 and CCL-2 (also known as MCP-1) are well-known chemo-attractants for neutrophils and monocytes, respectively. There was no detectable increase of other pro-inflammatory mediators such as CCL4, CCL5, IL1β or TNFα. To determine the contribution of ERK-phosphorylation in cytokine production, ERK1/2-phosphorylation was inhibited by using the MEK inhibitor PD98059 (51). The treatment abolished the UDP-glucose induced up regulation of IL-8 and CCL-2 (FIG. 8B). In addition, pretreatment of MDCK-C11 cells with the $P2Y_{14}$ antagonist PPTN (50) also abolished the increase in IL8 and CCl2 mRNA expression induced by UDP-glucose (FIG. 8C).

Figure 9:
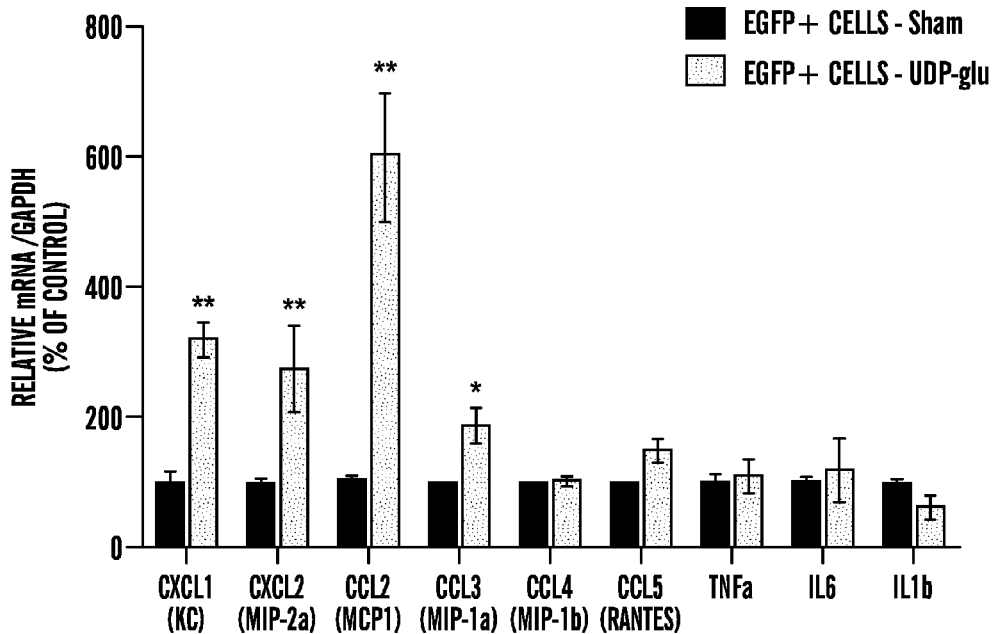
FIG. 9 shows quantitative PCR detection of pro-inflammatory mediators in EGFP(+) cells isolated by FACS from B1-EGFP mice 4 h after injection with saline (sham) or with saline containing 100 μM UDP-glucose (UDP-glu). All values are normalized to GAPDH. Data are represented as % changes relative to control. Values are mean±SEM (n=4), *P<0.05, ** P<0.001.

To determine whether $P2Y_{14}$ activation induces the upregulation of pro-inflammatory mRNAs in ICs in vivo, B1-EGFP mice were injected through the tail vein with either a saline solution (sham) or a solution containing 100 μM UDP-glucose. Kidneys were harvested 4 h later and processed for FACS isolation of EGFP(+) cells, mRNA extraction and real-time PCR to measure pro-inflammatory chemokine and cytokine expression. To avoid contamination of blood immune cells, which also express $P2Y_{14}$, the blood was flushed out of the kidneys by perfusing mice with PBS through the cardiac left ventricle. In addition, maximum purity (>95%) of EGFP(+) cells was obtained by further restricting the sorting parameters to isolate bright EGFP(+) cells. Cytospin smears of EGFP(+) cells immunostained for CD45 (a marker of leukocytes) did not show any contamination of the samples with leukocytes (data not shown). It was thus clear that any changes in pro-inflammatory mediator expression following P2Y14 activation with UDP-glucose were attributed to the presence of the receptor in ICs uniquely. As shown in FIG. 9, the neutrophil chemo-attractants, CXCL1 (KC) and CXCL2 (MIP-2α) (both homologues of the murine IL-8) had significantly higher expression levels following UDP-glucose treatment. A significant increase was also observed for the monocyte chemo-attractant CCL2 (MCP-1) and CCL3 (MIP-1α). No significant changes were observed for CCL4, CCL5, TNFα, IL1β, and IL6 expression. These results show that ICs produce pro-inflammatory mediators in vivo following activation by a pro-inflammatory agonist, and that this process can be efficiently promoted through UDP-glucose/P2Y$_{14}$ signaling.

UDP-Glucose Activation Induces Neutrophil Infiltration into the Kidney Medulla

Figure 10A:
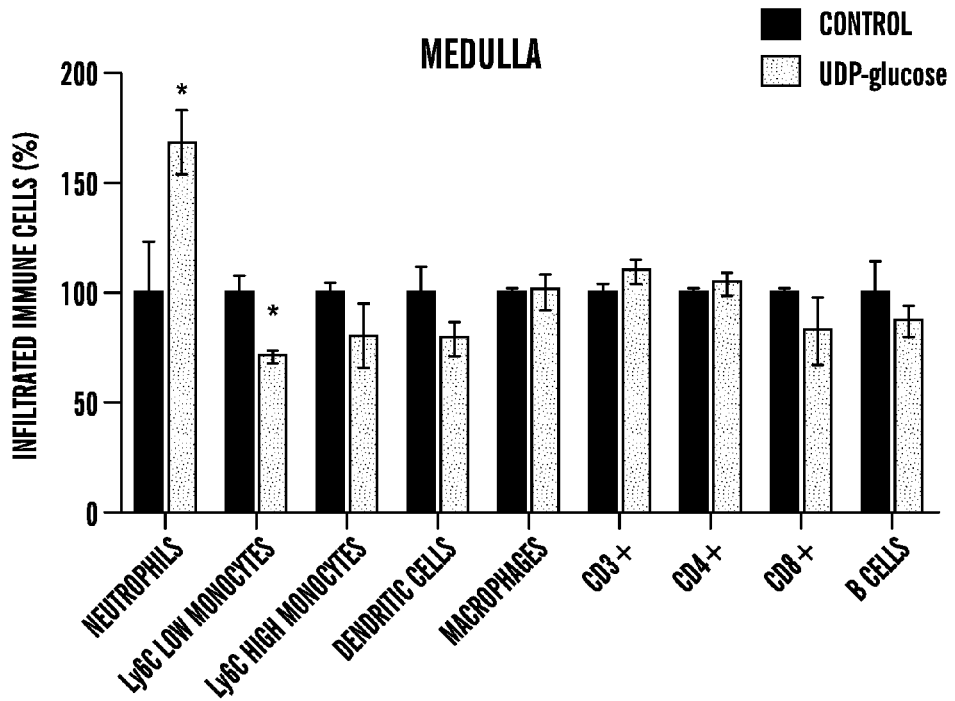
FIGS. 10A-10B show flow cytometry analysis of immune cell infiltration in the kidneys of mice 48 h after injection with saline (sham) or 100 μM UDP-glucose (UDP-glu). Changes in kidney medulla (FIG. 10A) or cortex (FIG. 10B) infiltrated immune cell counts are represented as % changes relative to control. Values are means of percent of each cell population±SEM from 4-6 animals. *P<0.05.
Figure 10B:
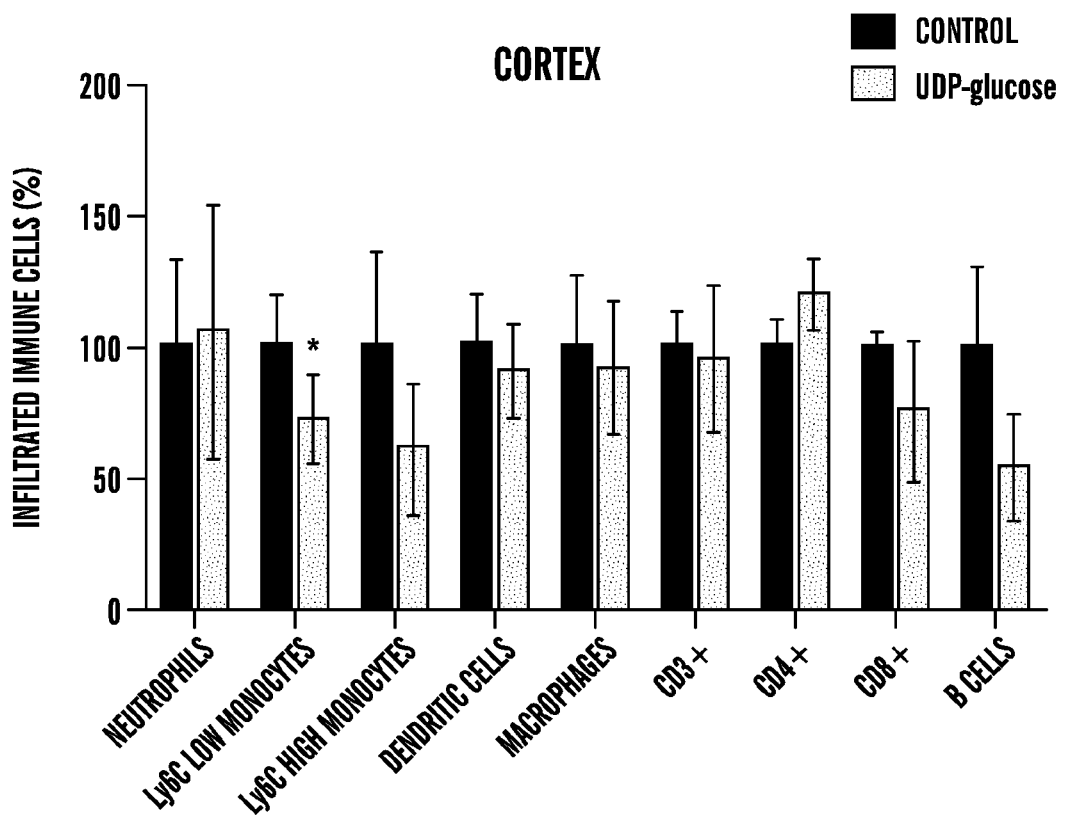

The pathophysiological relevance of P2Y$_{14}$ expression in ICs was assessed by measuring the infiltration of immune cells into the kidney using flow cytometry in mice that were challenged with an injection of UDP-glucose. To address the spatial distribution of immune cells in the kidney, the kidney was separated into cortex and medulla. B1-EGFP mice were challenged with a tail-vein injection of either 100 µM UDP-glucose (treated) or saline (sham), as discussed above. Mice were perfused 48 h later through the cardiac left ventricle with PBS to flush the blood out of the kidney vessels and hence measure only tissue infiltrated immune cells. This approach identified a significant and selective accumulation of neutrophils in the kidney medulla (FIG. 10A). This observation is consistent with the upregulation of neutrophil chemo-attractants observed in EGFP(+) cells after UDP-glucose activation. Anti-inflammatory (Ly6C low) monocytes also slightly decreased in the medulla, otherwise no significant changes in other immune cell counts were observed. In the kidney cortex, the numbers of most cell types remained unchanged upon UDP-glucose treatment, except for the Ly6C low monocyte population, which decreased slightly (FIG. 10B). No apparent changes in the number of infiltrated immune cells were observed in the cortex and medulla at earlier time points (12 and 24 hours) following UDP-glucose injection (data not shown).

Figure 11A:
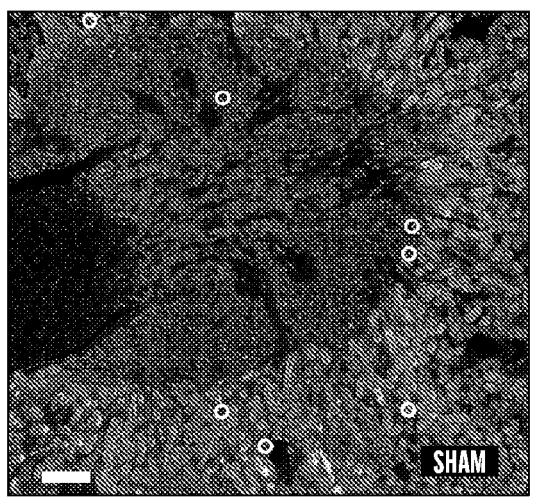
Figure 11B:
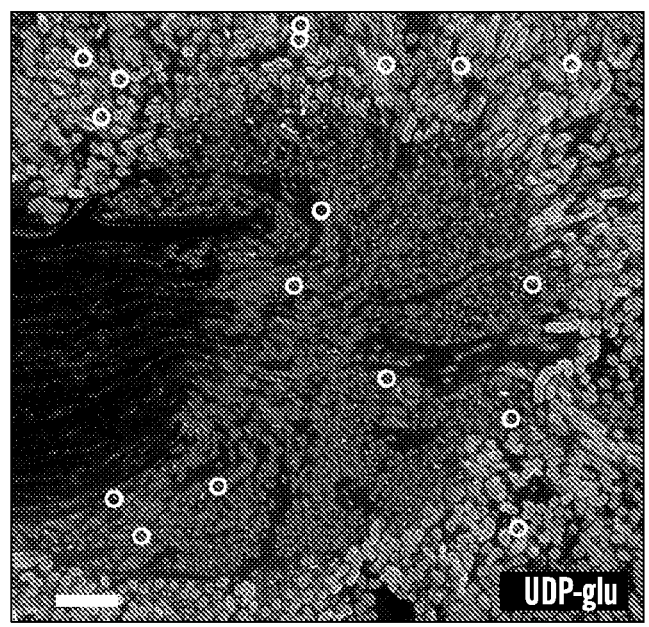
Figure 11E:
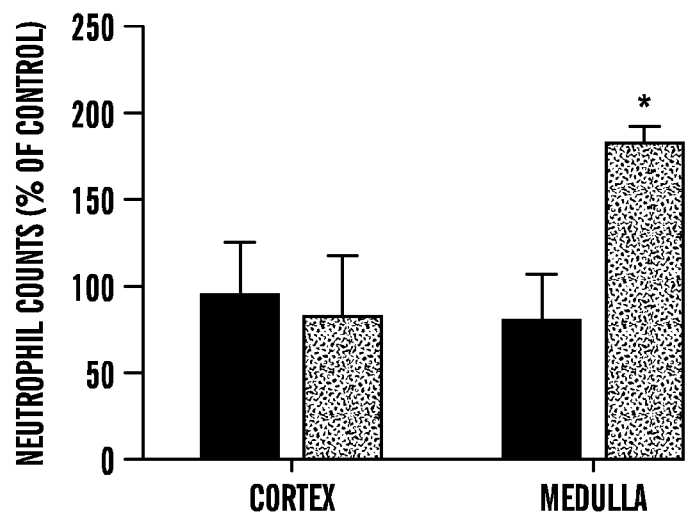

The UDP-Glucose Induced Neutrophil Infiltration Occurs Primarily in the Renal Medulla Kidney sections from control and UDP-glucose treated mice were stained for P2Y$_{14}$ (visualized as green) and for Ly6G, a neutrophil marker (visualized as red). Mosaic images were captured and neutrophils identified based on their positive labeling for Ly6G and their poly-nucleated phenotype (white circles) (FIGS. 11A-11B). More neutrophils were visible in the medulla of UDP-glucose treated mice (FIG. 11B) compared to sham-treated control mice (FIG. 11A). Higher magnification images show the presence of neutrophils in the renal medulla in UDP-glucose treated mice (FIGS. 11D, 11D', 11D") but not in controls (FIGS. 11C, 11C', 11C").

DISCUSSION

In this study, the P2 receptor profile of renal intercalated cells was characterized, and it was shown that they express high levels of the pro-inflammatory P2Y$_{14}$ receptor. In addition, the data provided herein demonstrate that P2Y$_{14}$ activation by UDP-glucose in ICs induces ERK1/2 phosphorylation followed by an inflammatory response mediated by chemokine upregulation and neutrophil recruitment into the kidney medulla. This study, therefore, identifies ICs as both sensors and mediators of sterile inflammation in the kidney.

While numerous P2 receptors were detected in mRNA samples isolated from the entire kidney, only 6 (P2X$_1$, P2X$_4$, P2X$_5$, P2Y$_2$, p2y5 and P2Y$_{14}$) receptors were found in ICs. The expression of P2Y$_2$ in these cells is in agreement with a previous pharmacological study showing functional P2Y$_2$ in the apical membrane of ICs in rabbit CCDs (52). P2Y$_2$ is traditionally viewed as a regulator of collecting duct principal cells, but these data further support its participation in IC function. Interestingly, while P2X$_7$ and P2X$_6$ have been described in collecting ducts (53, 54), these receptors were not detected in EGFP(+) cells, illustrating the importance of conducting cell-specific gene expression analysis. Among the receptors that were detected in ICs, P2X4 is regulated by extracellular pH (55) and it will be interesting to determine its role in the acidifying function of ICs.

The role of ICs in the defense against ascending pathogens has recently emerged by the discovery that they express the antimicrobial agent RNAse 7 and its modulator, the ribonuclease inhibitor (RI) (56-58). It was proposed that ICs are involved in the maintenance of luminal sterility in the kidney. Ascending pathogens induce renal epithelial cell damage (59-61). Uropathogenic *Escherichia coli* can adhere to the apical surface of medullary ICs, where it activates TLR4-dependent and independent signaling pathways (62). Multiple studies have characterized Toll-like receptors (TLR) as pathogen recognition and inflammation mediators in the kidney (62-64). In contrast to infection-induced inflammation, the molecular mechanisms that stimulate inflammation secondary to kidney diseases, nephrotoxicity and renal transplantation among others are poorly understood. Infection and ischemic kidney injury stimulate a potent inflammatory response including a rapid infiltration of neutrophils into the affected tissue (65). This present study provides evidence for a parallel non-TLR mediated inflammatory pathway determined by ICs. Without wishing to be bound by theory, the UDP-glucose released from damaged cells activates P2Y$_{14}$ receptor in ICs to initiate an inflammatory response via the production of pro-inflammatory chemokines, which then recruit neutrophils to damaged and/or infected areas. Without wishing to be bound by theory, P2Y$_{14}$ receptors act as danger sensors in kidney ICs. Intriguingly it was found that P2Y$_{14}$ mRNA expression is 20 times higher in medullary ICs compared to cortical ICs, despite the fact that immunostaining detected abundant protein in both cortical and medullary ICs. The renal medulla is the primary site of exposure to urinary ascending pathogens, which induce renal epithelial cell damage (59-61). The large amount of P2Y$_{14}$ mRNA seen in this region could be explained by the necessity to readily synthesize a functional protein immediately following infection, in order to induce a rapid inflammatory response. It could also reflect a higher level of mRNA expression in A-type ICs, which are enriched in the isolated medullary preparation compared to the cortical EGFP(+) cells.

P2Y$_{14}$ activates the MAPK pathway, which regulates the stability of IL-8 mRNA as opposed to LPS, which transcriptionally activates the IL-8 gene via the NF-kB pathway (66). In agreement with this notion, it was shown here that UDP-glucose administered both in vitro and in vivo induces a potent inflammatory response in ICs by up-regulating pro-inflammatory chemokine expression through MAPK activation and subsequent recruitment of neutrophils into the renal medulla. This would suggest that P2Y$_{14}$ (MAPK activation) and LPS (mainly NF-kB activation) act in parallel to increase IL-8 secretion and neutrophil recruitment.

Cytokines are released by leukocytes and renal tubular cells (67), and they are important contributors to the initiation of inflammation in the injured kidney. Pro-inflammatory cytokines such as TNFα, IL6 and IL1β induce chemokines through complementary activation, and the NF-kB and TLR related pathways. In this study it was shown that the increase in neutrophil and monocyte chemo-attractants is not accompanied by an increase of IL1β, TNFα or IL6, indicating that UDP-glucose can itself act as a pro-inflammatory mediator bypassing the cytokine effects. Without wishing to be bound by theory, by their ability to produce chemokines, ICs act as immune defense cells by creating a chemotaxic gradient favorable to neutrophil recruitment.

The increase in the amount of infiltrated neutrophils that was observed in the kidney medulla following UDP-glucose administration is in quantitative agreement with previous studies showing a 3-fold increase in renal neutrophil content after bilateral ischemia-reperfusion (67), and a 4-fold increase in the mouse uterus after UDP-glucose administration (33). In addition, significant neutrophil infiltration was found after 48 hours, a time course identical to the infiltration observed in the mouse uterus (33). Interestingly, a decrease in Ly6C low monocyte content following UDP-glucose administration was also observed. These cells have anti-inflammatory characteristics (68-70). Indeed a recent study suggested a role for Ly6C low monocytes as neutrophil recruiters in the presence of a "danger signal" in kidney blood vessels (71). This study showed that following TLR7 activation, the kidney endothelium retains crawling monocytes within the capillaries. Without wishing to be bound by theory, under basal conditions some of the crawling monocytes would eventually penetrate into the tissue whereas when a "danger signal" is sensed, the capillaries would retain the monocytes in order to recruit neutrophils, in which case the tissue infiltrated Ly6C low monocyte counts would decrease as indeed observed in this study.

In conclusion, the data provided herein show that ICs are DAMP sensors that mediate the recruitment of pro-inflammatory neutrophils to the kidney via activation of P2Y14. Almost all kidney diseases trigger a strong inflammatory response that can ultimately lead to kidney failure. The study presented herein, therefore, identifies P2Y14 as a useful therapeutic target for the, detection, prevention, or treatment of sterile inflammation in the kidney.

TABLE 1

| Gene | GeneBank accession | Forward primer (5'-3') | Reverse primer (5'-3') |
|---|---|---|---|
| Mouse P2rx1 | NM_008771 | AGGGTCTCAAACACCCACAG (SEQ ID NO: 1) | AGCTGTTCCAACCCACAGAG (SEQ ID NO: 2) |
| Mouse P2rx2 | NM_153400 | TTTGGCCCAACTTTGATCTC (SEQ ID NO: 3) | CCCAGAGCAAGATGCCTATC (SEQ ID NO: 4) |
| Mouse P2rx3 | NM_145526 | AGCCTCTTCTGGGACATCAA (SEQ ID NO: 5) | GTTAGGGATGGCGCTGAGTA (SEQ ID NO: 6) |
| Mouse P2rx4 | NM_011026 | AGCAGCTCTGTCCAAGCACT (SEQ ID NO: 7) | TCCGAGGACAACTTCTCTGG (SEQ ID NO: 8) |
| Mouse P2rx5 | NM_033321 | AAGGGGAGAGCAAACACTCA (SEQ ID NO: 9) | CACCAACCAAACAGCAAGTG (SEQ ID NO: 10) |
| Mouse P2rx6 | NM_011028 | GACGATCCTGGTCCAAGTGT (SEQ ID NO: 11) | ACCAGGAACTCCAAGGGTTT (SEQ ID NO: 12) |
| Mouse P2rx7 | NM_011027 | ACGCTTTCTTCAGCAGCAAT (SEQ ID NO: 13) | GCTGCTCTCAGTTCTGACCA (SEQ ID NO: 14) |
| Mouse P2ry1 | NM_008772 | GCATTTTGAGCCTTCTCAGG (SEQ ID NO: 15) | CTCCCTCCAGCCAAACAATA (SEQ ID NO: 16) |
| Mouse P2ry2 | NM_008773 | CAGCACAAACCATGCTGACT (SEQ ID NO: 17) | ACAAGGGACCTCCTGTCCTT (SEQ ID NO: 18) |
| Mouse P2ry4 | NM_020621 | CAGACCAAAGAGCACGAACA (SEQ ID NO: 19) | GCTGGAACAGCAATGGAACT (SEQ ID NO: 20) |
| Mouse P2ry5 | BC069991 | GGGCACTGAGAATTTTATCCA (SEQ ID NO: 21) | GAGCAGTCCCAGTGGCTTAG (SEQ ID NO: 22) |
| Mouse P2ry6 | NM_183168 | TAGGCCCTGGAATAGCAATG (SEQ ID NO: 23) | TCTTGGCAAATGGATGTGAA (SEQ ID NO: 24) |
| Mouse P2ry10 | NM_172435 | CAGAACCCCATCTTCTCAA (SEQ ID NO: 25) | GTGGTCCCTTCCTCTTCCTT (SEQ ID NO: 26) |
| Mouse P2ry12 | NM_027571 | AAAATGCCTGCTGCTTGAAT (SEQ ID NO: 27) | TGAAGAAATTCCAACAAAACGA (SEQ ID NO: 28) |
| Mouse P2ry13 | NM_028808 | AAGCCACAGAGGCAAGAGAA (SEQ ID NO: 29) | CCTGGAGTAAGGGACAGCAA (SEQ ID NO: 30) |
| Mouse P2ry14 | NM_133200 | CCATGCAAAATGGAAGTCTG (SEQ ID NO: 31) | CGGAAAGACTGGGTGTCTTC (SEQ ID NO: 32) |
| Mouse Gapdh | NM_008084.2 | GCACAGTCAAGGCCGAGAAT (SEQ ID NO: 33) | GCCTTCTCCATGGTGGTGAA (SEQ ID NO: 34) |

TABLE 1-continued

| Gene | GeneBank accession | Forward primer (5'-3') | Reverse primer (5'-3') |
|---|---|---|---|
| Mouse Slc26v1 | NM_011867.3 | TTAGCAATGTTCGGATGTGC (SEQ ID NO: 35) | GGCCAGCCTAACAGAGACAG (SEQ ID NO: 36) |
| Mouse Atp6v1b1 | NM_134157.2 | ACACGGCGCTCTAAATCAGT (SEQ ID NO: 37) | CCACCCACCTACACCAAAAG (SEQ ID NO: 38) |
| Mouse Slc4v1 | NM_011403.2 | TAGAAATGAGGGCAGGGA (SEQ ID NO: 39) | TGGCAAAACCTATTCCAA (SEQ ID NO: 40) |
| Mouse Cxcl1 | NM_008176.3 | TGTTGTGCGAAAAGAAGTGC (SEQ ID NO: 41) | CGAGACGAGACCAGGAGAAA (SEQ ID NO: 42) |
| Mouse Cxcl2 | NM_009140.2 | CGGTCAAAAAGTTTGCCTTG (SEQ ID NO: 43) | TCCAGGTCAGTTAGCCTTGC (SEQ ID NO: 44) |
| Mouse Tnf | NM_013693.2 | CCACCACGCTCTTCTGTCTAC (SEQ ID NO: 45) | AGGGTCTGGGCCATAGAACT (SEQ ID NO: 46) |
| Mouse Cc12 | NM_011333.3 | CAAGAAGGAATGGGTCCAGA (SEQ ID NO: 47) | AAGGCATCACAGTCCGAGTC (SEQ ID NO: 48) |
| Mouse Cc13 | NM_011337.2 | TAGCCACATCGAGGGACTCT (SEQ ID NO: 49) | ACCAACTGGGAGGGAGATG (SEQ ID NO: 50) |
| Mouse Cc14 | NM_013652.2 | GATTTCCTGCCCCTCTTCTT (SEQ ID NO: 51) | GGGAGACACGCGTCCTATAA (SEQ ID NO: 52) |
| Mouse Cc15 | NM_013653.3 | GTGCCCACGTCAAGGAGTAT (SEQ ID NO: 53) | CCACTTCTTCTCTGGGTTGG (SEQ ID NO: 54) |
| Mouse Il1h | NM_008361.3 | GGGCCTCAAAGGAAAGAATC (SEQ ID NO: 55) | TACCAGTTGGGGAACTCTGC (SEQ ID NO: 56) |
| Mouse Il6 | NM_031168.1 | GTGGCTAAGGACCAAGACCA (SEQ ID NO: 57) | ACCACAGTGAGGAATGTCCA (SEQ ID NO: 58) |
| Canine P2RX1 | XM_548344.2 | TTCGCTTTGACATTCTCGTG (SEQ ID NO: 59) | CATTTGCTCCGCATACTTGA (SEQ ID NO: 60) |
| Canine P2RX2 | XM_534633.3 | ACACTCTCCATCCTGCTGCT (SEQ ID NO: 61) | TGAGAGGAAGTCAGGGGAGA (SEQ ID NO: 62) |
| Canine P2RX3 | XM_540614.1 | GACTGTCCTCTGCGACATCA (SEQ ID NO: 63) | TTAGTGGCCGATGGAGTAGG (SEQ ID NO: 64) |
| Canine P2RX4 | XM_003639907.1 | CCACAGTCCTCATCAGAGCA (SEQ ID NO: 65) | GCCAGAGGTCACCTGAACAT (SEQ ID NO: 66) |
| Canine P2RX5 | XM_003639268.1 | GCCAGCCACTTCTCTTTGTC (SEQ ID NO: 67) | CAAATCCCACTCAGCCATTT (SEQ ID NO: 68) |
| Canine P2RX6 | XM_543562.1 | CTGGGTGTGATCACCTTCCT (SEQ ID NO: 69) | GAAGCTGGCTTTGTCTGCTC (SEQ ID NO: 70) |
| Canine P2RX7 | NM_001113456.1 | CCCACATTAGGATGGTGGAC (SEQ ID NO: 71) | CAGCCTGGACAAGTCTGTGA (SEQ ID NO: 72) |
| Canine P2RY1 | NM_001193673.1 | GCTTGTGAAGAGGCAGGAAC (SEQ ID NO: 73) | TCACTGGATCCACAGTCCAA (SEQ ID NO: 74) |
| Canine P2RY2 | XM_542321.2 | CGTCAACGTGGCTTACAAGA (SEQ ID NO: 75) | AATCCTCACTGCTGGTGGAC (SEQ ID NO: 76) |
| Canine P2RY4 | XM_003640257.1 | ATGTGAGCTCTGGCAGCTTT (SEQ ID NO: 77) | GGAAGCCACAGTGAGTGGAT (SEQ ID NO: 78) |
| Canine P2RY6 | XM_542320.1 | CTTCCTGCCCTTCCATGTTA (SEQ ID NO: 79) | GGCGGAACTTCTTCTGAGTG (SEQ ID NO: 80) |
| Canine P2RY10 | XM_549100.2 | GCACTGCGGATGGTTTTTAT (SEQ ID NO: 81) | CAGTGTGCTTTGGACAATGG (SEQ ID NO: 82) |
| Canine P2RY12 | NM_001003365.1 | CAAGAGGCGTAGGCAAAGTC (SEQ ID NO: 83) | GTAGGGAATGCGTGCAAAAT (SEQ ID NO: 84) |
| Canine P2RY14 | XM_542838.2 | CTCATTACAGCTGCCGATCA (SEQ ID NO: 85) | TCTAAAGGGCTGGCATAGGA (SEQ ID NO: 86) |

TABLE 1-continued

| Gene | GeneBank accession | Forward primer (5'-3') | Reverse primer (5'-3') |
|---|---|---|---|
| Canine GAPDH | NM_001003142.1 | GCCCTCAATGACCACTTTGT (SEQ ID NO: 87) | TCCTTGGAGGCCATGTAGAC (SEQ ID NO: 88) |
| Canine SLC26A4 | XM_540382.3 | AACTCCGAGCTTCCAGTCAA (SEQ ID NO: 89) | TCTCACTCCAACGACATCCA (SEQ ID NO: 90) |
| Canine ATP6V1B1 | XM_531858.3 | CAAATCTACCCTCCGGTCAA (SEQ ID NO: 91) | GGTTGATGAAGCTCCTCTCG (SEQ ID NO: 92) |
| Canine ATP6V0A4 | XM_539895.3 | CAGCCTTGTCTTCAACGTCA (SEQ ID NO: 93) | CTTGAGGTCGGTTCCCCTAT (SEQ ID NO: 94) |
| Canine SLC4A1 | NM_001048031.1 | TCATCCTCACTGTGCCTCTG (SEQ ID NO: 95) | CTCTGAGGCTCACACCTTCC (SEQ ID NO: 96) |
| Canine AQP2 | XM_543678.3 | GGGCTCCCTCCTCTACAACT (SEQ ID NO: 97) | GCAGCTCCACTGACTGTCG (SEQ ID NO: 98) |
| Canine IL8 | NM_001003200.1 | TCAATTGAACCGCAATCCTA (SEQ ID NO: 99) | TGCTTGTCGAGTTTTTGCTC (SEQ ID NO: 100) |
| Canine TNF | NM_001003244.4 | TCATCTTCTCGAACCCCAAG (SEQ ID NO: 101) | CTGGTTGTCTGTCAGCTCCA (SEQ ID NO: 102) |
| Canine CCL2 | NM_001003297.1 | CAAGAAAAGCCAAACCCAAA (SEQ ID NO: 103) | GAGGGCATTTAGGGAAGGTT (SEQ ID NO: 104) |
| Canine CCL3 | NM_001005251.1 | CAAGCCCGGTATTATCTTCG (SEQ ID NO: 105) | AGGCTTTCAGCTTCAGATCG (SEQ ID NO: 106) |
| Canine CCL4 | NM_001005250.1 | CTTTGAGACCAGCAGCCTCT (SEQ ID NO: 107) | CAGTTCAGTTCCAGATCATCCA (SEQ ID NO: 108) |
| Canine CCL5 | NM_001003010.2 | GCTCTGCAGTCAGGAAGGAG (SEQ ID NO: 109) | GGCTGAGAGGATAGCTGTGG (SEQ ID NO: 110) |
| Canine IL1B | NM_001037971.1 | CCTGTGTGATGAAGGATGGA (SEQ ID NO: 111) | TATATCCTGGCCACCTCTGG (SEQ ID NO: 112) |
| Canine IL6 | NM_001003301.1 | CTCGGCAAAATCTCTGCACT (SEQ ID NO: 113) | TGGAAGCATCCATCTTTTCC (SEQ ID NO: 114) |

References For Example 1

1. Arulkumaran, N., Turner, C. M., Sixma, M. L., Singer, M., Unwin, R., and Tam, F. W. 2013. Purinergic signaling in inflammatory renal disease. Front Physiol 4:194.
2. Burnstock, G., Evans, L. C., and Bailey, M. A. 2013. Purinergic signalling in the kidney in health and disease. Purinergic Signal. in press.
3. Praetorius, H. A., and Leipziger, J. 2010. Intrarenal purinergic signaling in the control of renal tubular transport. Annu Rev Physiol 72:377-393.
4. Rieg, T., and Vallon, V. 2009. ATP and adenosine in the local regulation of water transport and homeostasis by the kidney. Am J Physiol Regul Integr Comp Physiol 296: R419-427.
5. Vallon, V., Stockand, J., and Rieg, T. 2012. P2Y receptors and kidney function. Wiley Interdiscip Rev Membr Transp Signal 1:731-742.
6. Kishore, B. K., Nelson, R. D., Miller, R. L., Carlson, N. G., and Kohan, D. E. 2009. P2Y(2) receptors and water transport in the kidney. Purinergic Signal 5:491-499.
7. Breton, S., and Brown, D. 2013. Regulation of luminal acidification by the V-ATPase. Physiology (Bethesda) 28:318-329.
8. Wagner, C. A., Finberg, K. E., Breton, S., Marshansky, V., Brown, D., and Geibel, J. P. 2004. Renal Vacuolar H+-ATPase. Physiol. Rev. 84:1263-1314.
9. Belleannee, C., Da Silva, N., Shum, W. W., Brown, D., and Breton, S. 2010. Role of purinergic signaling pathways in V-ATPase recruitment to the apical membrane of acidifying epididymal clear cells. Am J Physiol Cell Physiol 298:C817-830.
10. Gallagher, J. A. 2004. ATP P2 receptors and regulation of bone effector cells. J Musculoskelet Neuronal Interact 4:125-127.
11. Kaunitz, J. D., and Yamaguchi, D. T. 2008. TNAP, TrAP, ecto-purinergic signaling, and bone remodeling. J Cell Biochem 105:655-662.
12. Li, Q., Schachter, J. B., Harden, T. K., and Nicholas, R. A. 1997. The 6H1 orphan receptor, claimed to be the p2y5 receptor, does not mediate nucleotide-promoted second messenger responses. Biochem Biophys Res Commun 236:455-460.
13. Lee, C. W., Rivera, R., Gardell, S., Dubin, A. E., and Chun, J. 2006. GPR92 as a new G12/13- and Gq-coupled lysophosphatidic acid receptor that increases cAMP, LPA5. J Biol Chem 281:23589-23597.
14. Murakami, M., Shiraishi, A., Tabata, K., and Fujita, N. 2008. Identification of the orphan GPCR, P2Y(10) receptor as the sphingosine-1-phosphate and lysophosphatidic acid receptor. Biochem Biophys Res Commun 371:707-712.
15. Freeman, K., Tsui, P., Moore, D., Emson, P. C., Vawter, L., Naheed, S., Lane, P., Bawagan, H., Herrity, N., Murphy, K., et al. 2001. Cloning, pharmacology, and tissue distribution of G-protein-coupled receptor GPR105 (KIAA0001) rodent orthologs. Genomics 78:124-128.
16. Chambers, J. K., Macdonald, L. E., Sarau, H. M., Ames, R. S., Freeman, K., Foley, J. J., Zhu, Y., McLaughlin, M. M., Murdock, P., McMillan, L., et al. 2000. A G protein-coupled receptor for UDP-glucose. J Biol Chem 275: 10767-10771.
17. Zimmermann, H. 2000. Extracellular metabolism of ATP and other nucleotides. Naunyn Schmiedebergs Arch Pharmacol 362:299-309.
18. Lazarowski, E. R., Shea, D. A., Boucher, R. C., and Harden, T. K. 2003. Release of cellular UDP-glucose as a potential extracellular signaling molecule. Mol Pharmacol 63:1190-1197.
19. Leipziger, J. 2011. Luminal nucleotides are tonic inhibitors of renal tubular transport. Curr Opin Nephrol Hypertens 20:518-522.
20. Chen, Y., Corriden, R., Inoue, Y., Yip, L., Hashiguchi, N., Zinkemagel, A., Nizet, V., Insel, P. A., and Junger, W. G. 2006. ATP release guides neutrophil chemotaxis via P2Y2 and A3 receptors. Science 314:1792-1795.
21. Elliott, M. R., Chekeni, F. B., Trampont, P. C., Lazarowski, E. R., Kadl, A., Walk, S. F., Park, D., Woodson, R. I., Ostankovich, M., Sharma, P., et al. 2009. Nucleotides released by apoptotic cells act as a find-me signal to promote phagocytic clearance. Nature 461:282-286.
22. Harden, T. K., Sesma, J. I., Fricks, I. P., and Lazarowski, E. R. 2010. Signalling and pharmacological properties of the P2Y receptor. Acta Physiol (Oxf) 199:149-160.
23. Chen, G. Y., and Nunez, G. 2010. Sterile inflammation: sensing and reacting to damage. Nat Rev Immunol 10:826-837.
24. Kono, H., and Rock, K. L. 2008. How dying cells alert the immune system to danger. Nat Rev Immunol 8:279-289.
25. Sesma, J. I., Esther, C. R., Jr., Kreda, S. M., Jones, L., O'Neal, W., Nishihara, S., Nicholas, R. A., and Lazarowski, E. R. 2009. Endoplasmic reticulum/golgi nucleotide sugar transporters contribute to the cellular release of UDP-sugar signaling molecules. J Biol Chem 284:12572-12583.
26. Lazarowski, E. R., Sesma, J. I., Seminario, L., Esther, C. R., Jr., and Kreda, S. M. 2011. Nucleotide release by airway epithelia. Subcell Biochem 55:1-15.
27. Dovlatova, N., Wijeyeratne, Y. D., Fox, S. C., Manolopoulos, P., Johnson, A. J., White, A. E., Latif, M. L., Ralevic, V., and Heptinstall, S. 2008. Detection of P2Y (14) protein in platelets and investigation of the role of P2Y(14) in platelet function in comparison with the EP(3) receptor. Thromb Haemost 100:261-270.
28. Gao, Z. G., Ding, Y., and Jacobson, K. A. 2010. UDP-glucose acting at P2Y14 receptors is a mediator of mast cell degranulation. Biochem Pharmacol 79:873-879.
29. Scrivens, M., and Dickenson, J. M. 2005. Functional expression of the P2Y14 receptor in murine T-lymphocytes. Br J Pharmacol 146:435-444.
30. Scrivens, M., and Dickenson, J. M. 2006. Functional expression of the P2Y14 receptor in human neutrophils. Eur J Pharmacol 543:166-173.
31. Okada, S. F., Zhang, L., Kreda, S. M., Abdullah, L. H., Davis, C. W., Pickles, R. J., Lazarowski, E. R., and Boucher, R. C. 2011. Coupled nucleotide and mucin hypersecretion from goblet-cell metaplastic human airway epithelium. Am J Respir Cell Mol Biol 45:253-260.
32. Muller, T., Bayer, H., Myrtek, D., Ferrari, D., Sorichter, S., Ziegenhagen, M. W., Zissel, G., Virchow, J. C., Jr., Luttmann, W., Norgauer, J., et al. 2005. The P2Y14 receptor of airway epithelial cells: coupling to intracellular Ca2+ and IL-8 secretion. Am J Respir Cell Mol Biol 33:601-609.
33. Arase, T., Uchida, H., Kajitani, T., Ono, M., Tamaki, K., Oda, H., Nishikawa, S., Kagami, M., Nagashima, T., Masuda, H., et al. 2009. The UDP-glucose receptor P2RY14 triggers innate mucosal immunity in the female reproductive tract by inducing IL-8. J Immunol 182:7074-7084.
34. Moore, D. J., Murdock, P. R., Watson, J. M., Faull, R. L., Waldvogel, H. J., Szekeres, P. G., Wilson, S., Freeman, K. B., and Emson, P. C. 2003. GPR105, a novel Gi/o-coupled UDP-glucose receptor expressed on brain glia and peripheral immune cells, is regulated by immunologic challenge: possible role in neuroimmune function. Brain Res Mol Brain Res 118:10-23.
35. Miller, R. L., Zhang, P., Smith, M., Beaulieu, V., Paunescu, T. G., Brown, D., Breton, S., and Nelson, R. D. 2005. V-ATPase B1-subunit promoter drives expression of EGFP in intercalated cells of kidney, clear cells of epididymis and airway cells of lung in transgenic mice. Am J Physiol Cell Physiol 288:C1134-1144.
36. Da Silva, N., Pisitkun, T., Belleannee, C., Miller, L. R., Nelson, R., Knepper, M. A., Brown, D., and Breton, S. 2010. Proteomic analysis of V-ATPase-rich cells harvested from the kidney and epididymis by fluorescence-activated cell sorting. Am J Physiol Cell Physiol 298: C1326-1342.
37. Vedovelli, L., Rothermel, J. T., Finberg, K. E., Wagner, C. A., Azroyan, A., Hill, E., Breton, S., Brown, D., and Paunescu, T. G. 2013. Altered V-ATPase expression in renal intercalated cells isolated from B1-subunit deficient mice by fluorescence activated cell sorting. Am J Physiol Renal Physiol 304:F522-F532.
38. Al-Awqati, Q., and Gao, X. B. 2011. Differentiation of intercalated cells in the kidney. Physiology (Bethesda) 26:266-272.
39. Brown, D., Bouley, R., Paunescu, T. G., Breton, S., and Lu, H. A. J. 2012. New insights into the dynamic regulation of water and acid-base balance by renal epithelial cells. Am. J. Physiol. Cell Physiol. 302:C1421-1433.
40. Brown, D., Hirsch, S., and Gluck, S. 1988. An H+-ATPase in opposite plasma membrane domains in kidney epithelial cell subpopulations. Nature 331:622-624.
41. Brown, D., Hirsch, S., and Gluck, S. 1988. Localization of a proton-pumping ATPase in rat kidney. J Clin Invest 82:2114-2126.
42. Nelson, R. D., Guo, X. L., Masood, K., Brown, D., Kalkbrenner, M., and Gluck, S. 1992. Selectively amplified expression of an isoform of the vacuolar H(+)-ATPase 56-kilodalton subunit in renal intercalated cells. Proc Natl Acad Sci USA 89:3541-3545.
43. Alper, S. L., Natale, J., Gluck, S., Lodish, H. F., and Brown, D. 1989. Subtypes of intercalated cells in rat kidney collecting duct defined by antibodies against erythroid band 3 and renal vacuolar H+-ATPase. Proc Natl Acad Sci USA 86:5429-5433.
44. Royaux, I. E., Wall, S. M., Karniski, L. P., Everett, L. A., Suzuki, K., Knepper, M. A., and Green, E. D. 2001. Pendrin, encoded by the Pendred syndrome gene, resides in the apical region of renal intercalated cells and mediates bicarbonate secretion. Proc Natl Acad Sci USA 98:4221-4226.

45. Wall, S. M., Hassell, K. A., Royaux, I. E., Green, E. D., Chang, J. Y., Shipley, G. L., and Verlander, J. W. 2003. Localization of pendrin in mouse kidney. Am J Physiol Renal Physiol 284:F229-241.
46. Fricks, I. P., Carter, R. L., Lazarowski, E. R., and Harden, T. K. 2009. Gi-dependent cell signaling responses of the human P2Y14 receptor in model cell systeMs. J Pharmacol Exp Ther 330:162-168.
47. Gekle, M., Wunsch, S., Oberleithner, H., and Silbernagl, S. 1994. Characterization of two MDCK-cell subtypes as a model system to study principal cell and intercalated cell properties. Pflugers Arch 428:157-162.
48. Krzeminski, P., Pomorski, P., and Baranska, J. 2008. The P2Y14 receptor activity in glioma C6 cells. Eur J Pharmacol 594:49-54.
49. Xu, J., Morinaga, H., Oh, D., Li, P., Chen, A., Talukdar, S., Mamane, Y., Mancini, J. A., Nawrocki, A. R., Lazarowski, E., et al. 2012. GPR105 ablation prevents inflammation and improves insulin sensitivity in mice with diet-induced obesity. J Immunol 189:1992-1999.
50. Barrett, M. O., Sesma, J. I., Ball, C. B., Jayasekara, P. S., Jacobson, K. A., Lazarowski, E. R., and Harden, T. K. 2013. A selective high-affinity antagonist of the P2Y14 receptor inhibits UDP-glucose-stimulated chemotaxis of human neutrophils. Mol Pharmacol 84:41-49.
51. Alessi, D. R., Cuenda, A., Cohen, P., Dudley, D. T., and Saltiel, A. R. 1995. PD 098059 is a specific inhibitor of the activation of mitogen-activated protein kinase kinase in vitro and in vivo. J Biol Chem 270:27489-27494.
52. Woda, C. B., Leite, M., Jr., Rohatgi, R., and Satlin, L. M. 2002. Effects of luminal flow and nucleotides on [Ca(2+)] (i) in rabbit cortical collecting duct. Am J Physiol Renal Physiol 283:F437-446.
53. Hillman, K. A., Burnstock, G., and Unwin, R. J. 2005. The P2X7 ATP receptor in the kidney: a matter of life or death? Nephron Exp Nephrol 101:e24-30.
54. Turner, C. M., Vonend, O., Chan, C., Burnstock, G., and Unwin, R. J. 2003. The pattern of distribution of selected ATP-sensitive P2 receptor subtypes in normal rat kidney: an immunohistological study. Cells Tissues Organs 175: 105-117.
55. Holzer, P. 2011. Acid sensing by visceral afferent neurones. Acta Physiol (Oxf) 201:63−75.
56. Spencer, J. D., Schwaderer, A. L., Dirosario, J. D., McHugh, K. M., McGillivary, G., Justice, S. S., Carpenter, A. R., Baker, P. B., Harder, J., and Hains, D. S. 2011. Ribonuclease 7 is a potent antimicrobial peptide within the human urinary tract. Kidney Int 80:174-180.
57. Spencer, J. D., Schwaderer, A. L., Eichler, T., Wang, H., Kline, J., Justice, S. S., Cohen, D. M., and Hains, D. S. 2013. An endogenous ribonuclease inhibitor regulates the antimicrobial activity of ribonuclease 7 in the human urinary tract. Kidney Int.
58. Spencer, J. D., Schwaderer, A. L., Wang, H., Bartz, J., Kline, J., Eichler, T., DeSouza, K. R., Sims-Lucas, S., Baker, P., and Hains, D. S. 2013. Ribonuclease 7, an antimicrobial peptide upregulated during infection, contributes to microbial defense of the human urinary tract. Kidney Int 83:615-625.
59. Chassin, C., Tourneur, E., Bens, M., and Vandewalle, A. 2011. A role for collecting duct epithelial cells in renal antibacterial defences. Cell Microbiol 13:1107-1113.
60. de Souza, R. M., and Olsburgh, J. 2008. Urinary tract infection in the renal transplant patient. Nat Clin Pract Nephrol 4:252-264.
61. Pelle, G., Vimont, S., Levy, P. P., Hertig, A., Ouali, N., Chassin, C., Arlet, G., Rondeau, E., and Vandewalle, A. 2007. Acute pyelonephritis represents a risk factor impairing long-term kidney graft function. Am J Transplant 7:899-907.
62. Chassin, C., Goujon, J. M., Darche, S., du Merle, L., Bens, M., Cluzeaud, F., Wefts, C., Ogier-Denis, E., Le Bouguenec, C., Buzoni-Gatel, D., et al. 2006. Renal collecting duct epithelial cells react to pyelonephritis-associated *Escherichia coli* by activating distinct TLR4-dependent and -independent inflammatory pathways. J Immunol 177:4773-4784.
63. Chassin, C., Hornef, M. W., Bens, M., Lotz, M., Goujon, J. M., Vimont, S., Arlet, G., Hertig, A., Rondeau, E., and Vandewalle, A. 2007. Hormonal control of the renal immune response and antibacterial host defense by arginine vasopressin. J Exp Med 204:2837-2852.
64. Chassin, C., Goujon, J. M., Le Bouguenec, C., Buzoni-Gatel, D., and Vandewalle, A. 2007. [A novel function for renal collecting duct intercalated cells: defense against uropathogenic *Escherichia coli*]. Med Sci (Paris) 23:32-34.
65. Bolisetty, S., and Agarwal, A. 2009. Neutrophils in acute kidney injury: not neutral any more. Kidney Int 75:674-676.
66. Hoffmann, E., Dittrich-Breiholz, O., Holtmann, H., and Kracht, M. 2002. Multiple control of interleukin-8 gene expression. J Leukoc Biol 72:847-855.
67. Awad, A. S., Rouse, M., Huang, L., Vergis, A. L., Reutershan, J., Cathro, H. P., Linden, J., and Okusa, M. D. 2009. Compartmentalization of neutrophils in the kidney and lung following acute ischemic kidney injury. Kidney Int 75:689-698.
68. Nahrendorf, M., Swirski, F. K., Aikawa, E., Stangenberg, L., Wurdinger, T., Figueiredo, J. L., Libby, P., Weissleder, R., and Pittet, M. J. 2007. The healing myocardium sequentially mobilizes two monocyte subsets with divergent and complementary functions. J Exp Med 204:3037-3047.
69. Hamers, A. A., Vos, M., Rassam, F., Marinkovic, G., Kurakula, K., van Gorp, P. J., de Winther, M. P., Gijbels, M. J., de Waard, V., and de Vries, C. J. 2012. Bone marrow-specific deficiency of nuclear receptor Nur77 enhances atherosclerosis. Circ Res 110:428-438.
70. Hanna, R. N., Shaked, I., Hubbeling, H. G., Punt, J. A., Wu, R., Herrley, E., Zaugg, C., Pei, H., Geissmann, F., Ley, K., et al. 2012. NR4A1 (Nur77) deletion polarizes macrophages toward an inflammatory phenotype and increases atherosclerosis. Circ Res 110:416-427.
71. Carlin, L. M., Stamatiades, E. G., Auffray, C., Hanna, R. N., Glover, L., Vizcay-Barrena, G., Hedrick, C. C., Cook, H. T., Diebold, S., and Geissmann, F. 2013. Nr4a1-Dependent Ly6C (low) Monocytes Monitor Endothelial Cells and Orchestrate Their Disposal. Cell 153:362-375.
72. Shum, W. W., Da Silva, N., Belleannee, C., McKee, M., Brown, D., and Breton, S. 2011. Regulation of V-ATPase recycling via a RhoA- and ROCKII-dependent pathway in epididymal clear cells. Am J Physiol Cell Physiol 301: C31-43.
73. Hurtado-Lorenzo, A., Skinner, M., El Annan, J., Futai, M., Sun-Wada, G. H., Bourgoin, S., Casanova, J., Wildeman, A., Bechoua, S., Ausiello, D. A., et al. 2006. V-ATPase interacts with ARNO and Arf6 in early endosomes and regulates the protein degradative pathway. Nat Cell Biol 8:124-136.
74. Paunescu, T. G., Jones, A. C., Tyszkowski, R., and Brown, D. 2008. V-ATPase expression in the mouse olfactory epithelium. Am J Physiol Cell Physiol 295: C923-930.

75. Azroyan, A., Marla, L., Crambert, G., Laghmani, K., Ramakrishnan, S., Edwards, A., and Doucet, A. 2012. Regulation of pendrin by cAMP: possible involvement in beta-adrenergic-dependent NaCl retention. Am J Physiol Renal Physiol 302:F1180-1187.
76. Brown, D., Lydon, J., McLaughlin, M., Stuart-Tilley, A., Tyszkowski, R., and Alper, S. 1996. Antigen retrieval in cryostat tissue sections and cultured cells by treatment with sodium dodecyl sulfate (SDS). Histochem Cell Biot 105:261-267.

Example 2

P2Y14 is Expressed in Human Kidney Intercalated Cells

Figure 12:
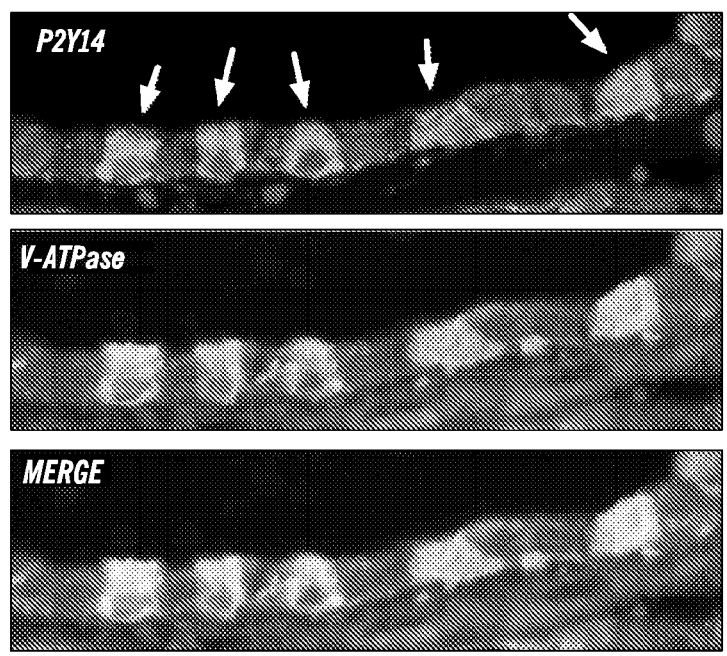
FIG. 12 is a set of images showing that P2Y14 is expressed in human kidney intercalated cells.
Figure 13:
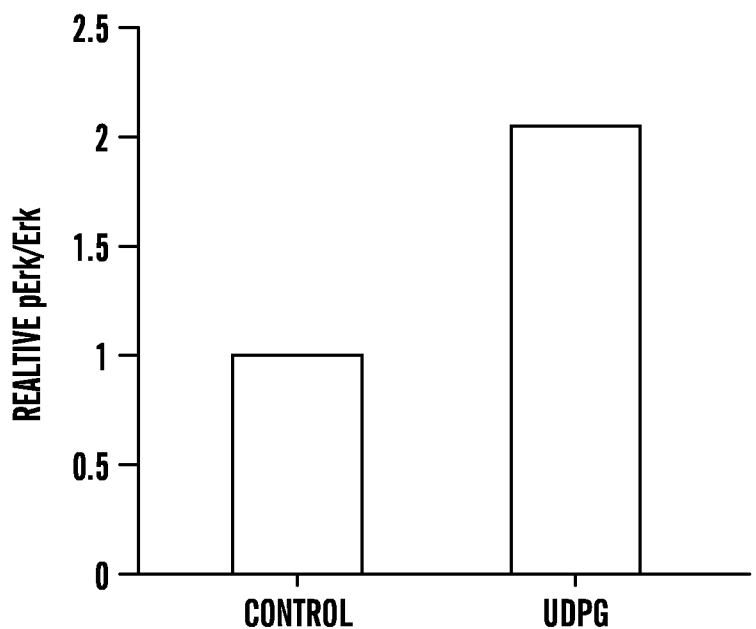
FIG. 13 is a bar graph showing that UDG-glucose increases ERK phosphorylation in ICs isolated by FACS.
Figure 14:
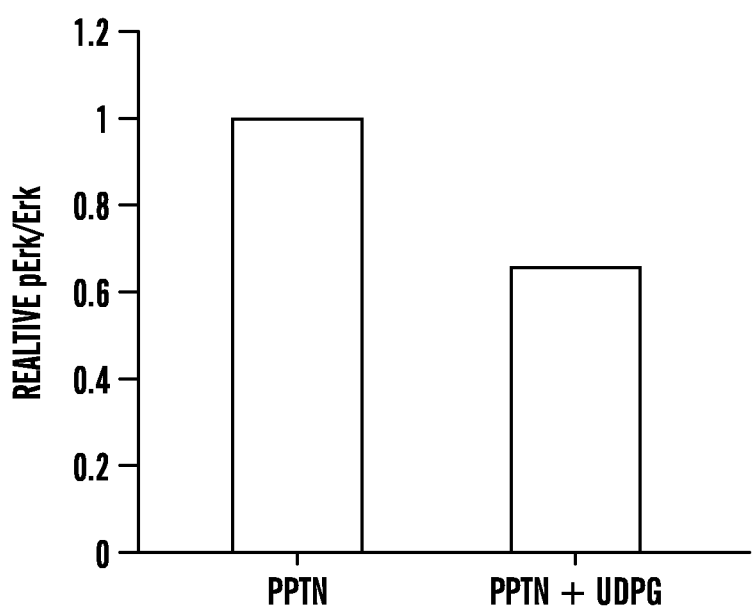
FIG. 14 is a bar graph showing that PPTN inhibits UDP-glucose dependent ERK phosphorylation in ICs isolated by FACS.

It is shown that P2Y14 is expressed in intercalated cells (ICs) from human kidney sections. ICs were identified by their positive labeling for the proton pump, V-ATPase (FIG. 12).

Measurement of UDP-Glucose in Mouse Urine Samples.

UDP-glucose in urine samples from mice was measured. Urine samples were collected in a paired manner in control mice, before and after UDP-glucose injection through their tail vein. The goal was to first determine the level of UDP-glucose in the urine of healthy mice, and then to determine the threshold at which neutrophil infiltration occurs in the kidney. A previously published protocol for the measurement of UDP-glucose in lung excretions was used (Barrett et al. Molec. Pharmacol. 2013). The data obtained show a very low UDP-glucose concentration under control conditions (30 nM range), and a significant increase (200 nM) after a single IV injection with a solution containing UDP-glucose.

UDP-Glucose Measurements in Human Urine Samples

UDP-glucose levels are measured in the urine samples from healthy individuals, as well as from patients with AKI, CKD and sepsis. UDP-glucose levels are also measured in a longitudinal study that examines patients who are admitted in the intensive care unit. Urine samples are collected every day in these patients, some of whom will develop AKI and some will not.

Murine Models of Kidney Disease

The novel pro-inflammatory function of ICs is explored in several murine disease models.

It was confirmed that the murine studies could be applied to human studies by showing expression of P2Y14 in human ICs in addition to murine ICs. It was also shown that very low levels of UDP-glucose were present in the urine of healthy mice, and that a single UDP-glucose challenge induced a significant increase in urine concentration.

What is claimed is:

1. A method of treating a subject determined to have a level of P2Y14 and/or UDP glucose above a reference level in a urine sample, the method comprising administering a treatment appropriate for treating renal inflammation.

2. The method of claim 1, wherein the treatment appropriate for treating renal inflammation comprises a P2Y14 inhibitor.

3. The method of claim 2, wherein the P2Y14 inhibitor is PPTN (4-[4-(piperidin-4-yl)phenyl]-7-[4-(trifluoromethyl)phenyl]-2-naphthoic acid) or an anti-P2Y14 antibody.

4. A method for treating renal inflammation in a subject, the method comprising:
   (a) measuring, in a urine sample obtained from a subject, a level of P2Y14,
   (b) comparing the level of P2Y14 with a reference level; and
   (c) administering a treatment appropriate for treating renal inflammation if the level of P2Y14 is above the reference level, thereby treating renal inflammation in the subject.

5. The method of claim 4, wherein the treatment comprises a P2Y14 inhibitor.

6. The method of claim 4, wherein the P2Y14 inhibitor is PPTN or an anti-P2Y14 antibody.

7. The method of claim 4, wherein the level of P2Y14 is a protein level of P2Y14 or the level of a nucleic acid encoding P2Y14.

8. The method of claim 7, wherein the protein level of P2Y14 is measured by an immunoassay.

9. The method of claim 8, wherein the sample is contacted with an anti-P2Y14 antibody.

10. The method of claim 1, wherein the treatment prevents onset of acute kidney injury (AKI).

11. The method of claim 1, wherein the method detects early stage inflammation.

12. A method for treating renal inflammation in a subject, the method comprising:
   (a) measuring, in a urine sample obtained from a subject, a level of UDP-glucose,
   (b) comparing the level of UDP-glucose with a reference level; and
   (c) administering a treatment appropriate for treating renal inflammation if the level of UDP-glucose is above the reference level, thereby treating renal inflammation in the subject.

13. The method of claim 12, wherein the treatment comprises a P2Y14 inhibitor.

14. The method of claim 13, wherein the P2Y14 inhibitor is PPTN or an anti-P2Y14 antibody.

15. The method of claim 12, wherein the treatment prevents onset of acute kidney injury (AKI).

16. The method of claim 12, wherein the method detects early stage inflammation.

17. A method of monitoring treatment progress in a subject suffering from renal inflammation, the method comprising:
   (a) measuring at a first time point, a first level of P2Y14 and/or UDP-glucose in a first urine sample obtained from the subject;
   (b) administering to the subject a therapeutic agent for treating renal inflammation; and
   (c) measuring, at a second time point, a second level of P2Y14 and/or UDP-glucose in a second urine sample obtained from the subject, wherein the second time point is later than the first time point and after said administration, and wherein if the second level is significantly lower than the first level, then the treatment is considered to be effective.

18. The method of claim 17, wherein the therapeutic agent is a P2Y14 inhibitor.

19. A method for preventing acute kidney injury (AKI), the method comprising administering a therapeutic appropriate for the treatment of renal inflammation to a subject determined to have a level of P2Y14 and/or UDP glucose above a reference level in a urine sample, thereby preventing acute kidney injury.

* * * * *

UNITED STATES PATENT AND TRADEMARK OFFICE
CERTIFICATE OF CORRECTION

| | | |
|---|---|---|
| PATENT NO. | : 9,891,236 B2 | Page 1 of 1 |
| APPLICATION NO. | : 15/035033 | |
| DATED | : February 13, 2018 | |
| INVENTOR(S) | : Breton et al. | |

It is certified that error appears in the above-identified patent and that said Letters Patent is hereby corrected as shown below:

In the Specification

At Column 1, Line 16:
Insert the following heading and paragraph:
--GOVERNMENT SUPPORT
This invention was made with government support under DK097124 awarded by the National Institutes of Health. The government has certain rights in the invention.--

Signed and Sealed this
Second Day of May, 2023

Katherine Kelly Vidal
*Director of the United States Patent and Trademark Office*